US010912508B2

United States Patent
Flax et al.

(10) Patent No.: US 10,912,508 B2
(45) Date of Patent: *Feb. 9, 2021

(54) METHOD AND SYSTEM FOR ASSESSING MENTAL STATE

(71) Applicant: Medibio Limited, South Yarra (AU)

(72) Inventors: Matthew Flax, Leichhardt (AU); Aaron Wong, Warabrook (AU); Michael Player, Randwick (AU); Todd Jolly, Merewether (AU); Hans Stampfer, Mount Lawley (AU)

(73) Assignee: MEDIBIO LIMITED, Sydney (AU)

( * ) Notice: Subject to any disclaimer, the term of this patent is extended or adjusted under 35 U.S.C. 154(b) by 56 days.

This patent is subject to a terminal disclaimer.

(21) Appl. No.: 15/736,652

(22) PCT Filed: Jun. 15, 2016

(86) PCT No.: PCT/AU2016/050490
§ 371 (c)(1),
(2) Date: Dec. 14, 2017

(87) PCT Pub. No.: WO2016/201499
PCT Pub. Date: Dec. 22, 2016

(65) Prior Publication Data
US 2018/0184961 A1 Jul. 5, 2018

Related U.S. Application Data

(60) Provisional application No. 62/175,796, filed on Jun. 15, 2015.

(51) Int. Cl.
*A61B 5/16* (2006.01)
*G06N 20/00* (2019.01)
(Continued)

(52) U.S. Cl.
CPC ............ *A61B 5/165* (2013.01); *A61B 5/0022* (2013.01); *A61B 5/024* (2013.01); *A61B 5/4809* (2013.01);
(Continued)

(58) Field of Classification Search
CPC ..... A61B 5/165; A61B 5/0022; A61B 5/4812; A61B 5/7264; A61B 5/7246;
(Continued)

(56) References Cited

U.S. PATENT DOCUMENTS 4,753,246 A 6/1988 Freeman
4,779,100 A 10/1988 Voelz
(Continued)

FOREIGN PATENT DOCUMENTS

CN 1251974 A 5/2000
CN 101060809 A 10/2007
(Continued)

OTHER PUBLICATIONS

International Preliminary Report on Patentability and Written Opinion of the International Searching Authority (Forms PCT/IB/326, PCT/IB/373 and PCT/ISA/237) for Application No. PCT/AU2016/050490, dated Dec. 28, 2017.
(Continued)

*Primary Examiner* — Rex R Holmes
(74) *Attorney, Agent, or Firm* — Birch, Stewart, Kolasch & Birch, LLP

(57) ABSTRACT

A computer-implemented method of assessing a mental state of a subject (106) includes receiving (302), as input, a heartbeat record (200) of the subject. The heartbeat record comprises a sequence of heartbeat data samples obtained over a time span which includes a pre-sleep period (208), a sleep period (209) having a sleep onset time (224) and a sleep conclusion time (226), and a post-sleep period (210).
(Continued)

At least the sleep onset time and the sleep conclusion time are identified (304) within the heartbeat record. A knowledge base (124) is then accessed (306), which comprises data obtained via expert evaluation of a training set of subjects and which embodies a computational model of a relationship between mental state and heart rate characteristics. Using information in the knowledge base, the computational model is applied (308) to compute at least one metric associated with the mental state of the subject, and to generate an indication of mental state based upon the metric. The indication of mental state is provided (310) as output.

13 Claims, 11 Drawing Sheets

(51) Int. Cl.
  *A61B 5/024* (2006.01)
  *A61B 5/00* (2006.01)
  *G16H 40/63* (2018.01)
  *G16H 10/65* (2018.01)

(52) U.S. Cl.
  CPC .......... *A61B 5/4812* (2013.01); *A61B 5/7246* (2013.01); *A61B 5/7264* (2013.01); *A61B 5/7267* (2013.01); *G06N 20/00* (2019.01); *G16H 10/65* (2018.01); *G16H 40/63* (2018.01)

(58) Field of Classification Search
  CPC ..... A61B 5/7267; A61B 5/4809; A61B 5/024; G06N 20/00; G16H 40/63; G16H 10/65
  See application file for complete search history.

(56) References Cited

U.S. PATENT DOCUMENTS

| | | | |
|---|---|---|---|
| 4,800,893 A | 1/1989 | Ross et al. | |
| 4,832,038 A | 5/1989 | Arai et al. | |
| 4,896,675 A | 1/1990 | Ohsuga et al. | |
| 5,280,793 A | 1/1994 | Rosenfeld | |
| 5,577,510 A | 11/1996 | Chittum et al. | |
| 5,871,517 A | 2/1999 | Abrams et al. | |
| 6,245,021 B1 | 6/2001 | Stampfer | |
| 6,942,622 B1 | 9/2005 | Turcott | |
| 7,640,055 B2 | 12/2009 | Geva et al. | |
| 7,689,437 B1 | 3/2010 | Teller et al. | |
| 8,306,610 B2 | 11/2012 | Mirow | |
| 8,369,936 B2 | 2/2013 | Farringdon et al. | |
| 8,452,387 B2 | 5/2013 | Osorio et al. | |
| 8,568,330 B2 * | 10/2013 | Mollicone | A61B 5/024 600/508 |
| 8,679,009 B2 | 3/2014 | Osorio | |
| 8,744,562 B2 | 6/2014 | Giftakis et al. | |
| 9,075,910 B2 | 7/2015 | Bhavaraju et al. | |
| 9,396,486 B2 | 7/2016 | Stivoric et al. | |
| 2002/0002327 A1 | 1/2002 | Grant et al. | |
| 2004/0111033 A1 | 6/2004 | Oung et al. | |
| 2004/0236236 A1 | 11/2004 | Yanagidaira et al. | |
| 2005/0148897 A1 | 7/2005 | Cho et al. | |
| 2005/0245790 A1 | 11/2005 | Bergfalk et al. | |
| 2008/0033304 A1 | 2/2008 | Dalal et al. | |
| 2008/0167565 A1 | 7/2008 | Laitio et al. | |
| 2009/0149778 A1 * | 6/2009 | Naujokat | A61B 5/0002 600/595 |
| 2009/0157662 A1 | 6/2009 | Suffin et al. | |
| 2009/0192399 A1 | 7/2009 | Choi et al. | |
| 2009/0292180 A1 | 11/2009 | Mirow | |
| 2010/0069762 A1 | 3/2010 | Mietus et al. | |
| 2010/0113893 A1 | 5/2010 | Cohen et al. | |
| 2010/0217099 A1 | 8/2010 | LeBoeuf et al. | |
| 2010/0280335 A1 | 11/2010 | Carlson | |
| 2011/0112442 A1 | 5/2011 | Meger et al. | |
| 2011/0178814 A1 | 7/2011 | McGlennen et al. | |
| 2011/0184298 A1 | 7/2011 | De Marchena et al. | |
| 2012/0232414 A1 | 9/2012 | Mollicone et al. | |
| 2013/0079602 A1 | 3/2013 | Picard et al. | |
| 2013/0245396 A1 | 9/2013 | Berman et al. | |
| 2013/0262155 A1 | 10/2013 | Hinkamp | |
| 2013/0296730 A1 | 11/2013 | Osorio et al. | |
| 2014/0031651 A1 | 1/2014 | Chon | |
| 2014/0046144 A1 | 2/2014 | Jayaraman et al. | |
| 2014/0058279 A1 | 2/2014 | Shinba | |
| 2014/0081090 A1 | 3/2014 | Picard et al. | |
| 2014/0088378 A1 | 3/2014 | Muzet | |
| 2014/0115008 A1 | 4/2014 | Stivoric et al. | |
| 2014/0122496 A1 | 5/2014 | Stivoric et al. | |
| 2014/0122537 A1 | 5/2014 | Stivoric et al. | |
| 2014/0136450 A1 | 5/2014 | Lee | |
| 2014/0180020 A1 | 6/2014 | Stivoric et al. | |
| 2014/0180022 A1 | 6/2014 | Stivoric et al. | |
| 2014/0180598 A1 | 6/2014 | Stivoric et al. | |
| 2014/0200414 A1 | 7/2014 | Osorio | |
| 2014/0206945 A1 | 7/2014 | Liao | |
| 2014/0206946 A1 | 7/2014 | Kim et al. | |
| 2014/0213854 A1 | 7/2014 | Stivoric et al. | |
| 2014/0213856 A1 | 7/2014 | Teller et al. | |
| 2014/0213857 A1 | 7/2014 | Teller et al. | |
| 2014/0213938 A1 | 7/2014 | Stivoric et al. | |
| 2014/0214836 A1 | 7/2014 | Stivoric et al. | |
| 2014/0220525 A1 | 8/2014 | Stivoric et al. | |
| 2014/0221730 A1 | 8/2014 | Stivoric et al. | |
| 2014/0221773 A1 | 8/2014 | Stivoric et al. | |
| 2014/0221774 A1 | 8/2014 | Teller et al. | |
| 2014/0221775 A1 | 8/2014 | Stivoric et al. | |
| 2014/0221776 A1 | 8/2014 | Stivoric et al. | |
| 2014/0221780 A1 | 8/2014 | Goldberger et al. | |
| 2014/0221789 A1 | 8/2014 | Pacione et al. | |
| 2014/0221790 A1 | 8/2014 | Pacione et al. | |
| 2014/0221791 A1 | 8/2014 | Pacione et al. | |
| 2014/0221849 A1 | 8/2014 | Farringdon et al. | |
| 2014/0221850 A1 | 8/2014 | Farringdon et al. | |
| 2014/0222732 A1 | 8/2014 | Stivoric et al. | |
| 2014/0222733 A1 | 8/2014 | Stivoric et al. | |
| 2014/0222734 A1 | 8/2014 | Stivoric et al. | |
| 2014/0222735 A1 | 8/2014 | Stivoric et al. | |
| 2014/0222847 A1 | 8/2014 | Stivoric et al. | |
| 2014/0240124 A1 | 8/2014 | Bychkov | |
| 2014/0275854 A1 | 9/2014 | Venkatraman et al. | |
| 2014/0308636 A1 | 10/2014 | Stivoric et al. | |
| 2014/0308639 A1 | 10/2014 | Stivoric et al. | |
| 2014/0309939 A1 | 10/2014 | Stivoric et al. | |
| 2014/0309940 A1 | 10/2014 | Stivoric et al. | |
| 2014/0310105 A1 | 10/2014 | Stivoric et al. | |
| 2014/0310294 A1 | 10/2014 | Stivoric et al. | |
| 2014/0310298 A1 | 10/2014 | Stivoric et al. | |
| 2014/0316230 A1 | 10/2014 | Denison et al. | |
| 2014/0316885 A1 | 10/2014 | Stivoric et al. | |
| 2014/0317039 A1 | 10/2014 | Stivoric et al. | |
| 2014/0317042 A1 | 10/2014 | Stivoric et al. | |
| 2014/0317119 A1 | 10/2014 | Stivoric et al. | |
| 2014/0317135 A1 | 10/2014 | Stivoric et al. | |
| 2014/0342328 A1 | 11/2014 | Pacione et al. | |
| 2014/0344282 A1 | 11/2014 | Stivoric et al. | |
| 2015/0025403 A1 | 1/2015 | Chang et al. | |
| 2015/0099987 A1 | 4/2015 | Bhatkar et al. | |
| 2015/0126890 A1 | 5/2015 | Scheib | |
| 2015/0126891 A1 | 5/2015 | Scheib | |
| 2015/0142553 A1 | 5/2015 | Kodra et al. | |
| 2015/0148621 A1 | 5/2015 | Sier | |
| 2015/0150516 A1 | 6/2015 | Tochikubo et al. | |
| 2015/0182129 A1 | 7/2015 | Colley et al. | |
| 2015/0208986 A1 | 7/2015 | Gottesman | |
| 2015/0282722 A1 | 10/2015 | Klepp | |
| 2015/0289809 A1 | 10/2015 | Pacione et al. | |
| 2015/0289810 A1 | 10/2015 | Pacione et al. | |
| 2015/0313529 A1 * | 11/2015 | Nevo | A61B 5/165 600/595 |
| 2015/0374301 A1 | 12/2015 | Teller et al. | |
| 2016/0015318 A1 | 1/2016 | Bhavaraju et al. | |
| 2016/0113567 A1 | 4/2016 | Osvath et al. | |
| 2016/0310022 A1 | 10/2016 | Stivoric et al. | |
| 2016/0317073 A1 | 11/2016 | Brockway et al. | |

(56) References Cited

U.S. PATENT DOCUMENTS

| | | |
|---|---|---|
| 2016/0338640 A1 | 11/2016 | Chan et al. |
| 2016/0338641 A1 | 11/2016 | Chan et al. |
| 2016/0375245 A1 | 12/2016 | Frei et al. |
| 2016/0379505 A1 | 12/2016 | el Kaliouby et al. |
| 2017/0035365 A1 | 2/2017 | Hasegawa et al. |
| 2017/0071546 A1 | 3/2017 | Jain et al. |
| 2017/0127993 A1 | 5/2017 | Olivier et al. |

FOREIGN PATENT DOCUMENTS

| | | |
|---|---|---|
| CN | 104127193 A | 11/2014 |
| CN | 104127194 A | 11/2014 |
| EP | 0504945 A2 | 9/1992 |
| FR | 2501996 A1 | 9/1982 |
| GB | 2185815 A | 7/1987 |
| JP | 60-54836 A | 3/1985 |
| JP | 10-5201 A | 1/1998 |
| WO | WO 9608992 A2 | 3/1996 |
| WO | WO 2008/094125 A1 | 8/2008 |
| WO | WO 2014/064580 A1 | 5/2014 |

OTHER PUBLICATIONS

Rao et al., "Circadian rhythm of vital signs, norepinephrine, epinephrine, thyroid hormones, and cortisol in schizophrenia," Psychiatry Research, vol. 57, No. 1, Jun. 29, 1995, pp. 21-39.

Taillard et al., "Heart rate orcadian rhythm as a biological marker of desynchronization in major depression: A methodological and preliminary report," Chronobiology International, vol. 7, No. 4, 1990 (published online Aug. 7, 2009), pp. 305-316 (13 pages total).

Tulen et al., "Anxiety and autonomic regulation in major depressive disorder: an exploratory study," Journal of Affective Disorders, vol. 40, 1996, pp. 61-71.

Extended European Search Report issued in EP Application No. 16810612.8 dated Nov. 30, 2018.

Wang Jenn-Shing et al.—"A k-nearest-neighbor classifier with heart rate variability feature-based transformation algorithm for driving stress recognition," Neurocomputing, Elsevier, Amsterdam, NL vol. 116, Oct. 8, 2012, pp. 136-143.

Written Opinion of the International Searching Authority and International Search Report (Forms PCT/ISA/237 and PCT/ISA/210), dated Sep. 12, 2016, for International Application No. PCT/AU2016/050491.

Written Opinion of the International Searching Authority and International Search Report (Forms PCT/ISA/237 and PCT/ISA/210), dated Sep. 21, 2016, for International Application No. PCT/AU2016/050490.

\* cited by examiner

METHOD AND SYSTEM FOR ASSESSING MENTAL STATE

CROSS REFERENCE TO RELATED APPLICATIONS

This application is the National Phase of PCT International Application No. PCT/AU2016/050490, filed on Jun. 15, 2016, which claims priority under 35 U.S.C. 119(e) to U.S. Provisional Application No. 62/175,796, filed on Jun. 15, 2015, all of which are hereby expressly incorporated by reference into the present application.

FIELD OF THE INVENTION

The present invention relates generally to the field of mental health care, and more particularly to methods and systems, along with associated hardware and software components, for objectively assessing the state of mental health of an individual. Embodiments of the invention may usefully assist health care professionals, and others, in identifying and/or treating individuals who may be suffering from, recovering from, or at risk of, adverse mental health conditions such as depression.

BACKGROUND TO THE INVENTION

It is estimated that one in four citizens of developed nations will experience a mental health problem during their lifetime, with up to 10 percent of the population experiencing some type of depressive or anxiety-related disorder every year. The global economic cost of mental illness is measured in trillions of dollars annually.

Presently, there is no accepted and widely recognised objective test for many mental illnesses, such as depression. The diagnostic 'gold standard' in such cases remains clinical/expert assessment and opinion, based upon interviews with the patient along with close friends and family, and self-reporting (e.g. through the completion of questionnaires), for comparison against clinical symptoms catalogued in the Diagnostic and Statistical Manual of Mental Disorders (currently DSM-5).

However, due to the subjective nature of many aspects of this diagnostic process, agreement between clinicians can vary considerably, even for high-prevalence disorders such as depression and anxiety.

There is, accordingly, a need for quantitative, objective tests that can be employed by clinicians when diagnosing psychological disorders, and for monitoring the progress of patients undergoing treatment. Ideally, such tests should be simple, safe and unobtrusive, so that they can be undertaken without significant impact on the patient's lifestyle or day-to-day routine.

Provision of objective tests for mental health would enable numerous significant benefits to be realised. Better objective information could lead to earlier diagnosis, earlier intervention, and better outcomes for patients. Ongoing monitoring of patients could provide an objective indication of therapeutic effectiveness, enabling treatments to be varied and optimised based upon patient response. These improvements in treatment and outcomes would result in savings to the health system, and to the community in general.

It has been known for some time that there is a relationship between circadian heart rate patterns and psychological state. For example, U.S. Pat. No. 6,245,021 describes the use of recorded 24-hour heart rate patterns in the diagnosis of psychological disorders including depression, anxiety, panic disorder, obsessive compulsive disorder (OCD) and schizophrenia. However, the procedures disclosed in this patent still require expert (i.e. human) review of circadian heart rate patterns, by clinicians with the necessary training and experience to identify features that are commonly associated with the different disorders. Patients are required to maintain a daily diary, which enables the clinician to compare features in the heart rate patterns against activity (e.g. exercise) in which the patient may have engaged, so as to avoid misinterpreting these features. Clearly, a system that requires 24-hour monitoring, and the keeping of a daily diary, has a noticeable impact upon the patient's lifestyle and day-to-day routine, leading to a greater likelihood of non-compliance with the measurement and monitoring regime.

Accordingly, it would be desirable to develop new and objective methods and systems to assist in identifying individuals who may be suffering from, or at risk of, adverse mental health conditions such as depression, and which are able to provide one or more of the benefits discussed above. The present invention has been devised in order to address this need.

SUMMARY OF THE INVENTION

In one aspect, the present invention provides a computer-implemented method of assessing a mental state of a subject, the method comprising:

receiving, as input, a heartbeat record of the subject, which comprises a sequence of heartbeat data samples obtained over a time span which includes a pre-sleep period, a sleep period having a sleep onset time and a sleep conclusion time, and a post-sleep period;

identifying, within the heartbeat record, at least the sleep onset time and the sleep conclusion time;

accessing a knowledge base comprising data obtained via expert evaluation of a training set of subjects and embodying a computational model of a relationship between mental state and heart rate characteristics;

using information in the knowledge base, applying the computational model to compute at least one metric associated with the mental state of the subject, and to generate an indication of mental state based upon the metric; and providing, as output, the indication of mental state.

Embodiments of the invention may comprise expert systems in which the knowledge base contains information generated via machine-learning methodologies. For example, the knowledge base may embody measured heart rate data for a plurality of subjects comprising the training set, along with the results of expert assessment of each subject in the training set. In such embodiments, the knowledge base captures salient information regarding the relationship between the mental state of each subject in the training set, and measured heart rate characteristics, in a form such that a corresponding computational model may be employed to predict the expert assessment of subsequent unseen test subjects.

According to embodiments of the invention, the indication of mental state comprises an indication of mental health of the subject. For example, the indication of mental state may distinguish between a nominally normal (i.e. relatively healthy) condition, a nominally depressed condition, and/or one or more other conditions. The other conditions may be indeterminate, or may be conditions such as stress or anxiety. In any event, the output indication of mental health may not be regarded as a diagnosis, but may be useful to health care practitioners—and especially to those practitioners who are not themselves experts in mental health—in identifying individuals who may be suffering from, or at risk of, adverse mental health conditions. Such individuals may then be referred to an appropriate health care professional for further review, tests, diagnosis and/or treatment.

Identifying the sleep onset and conclusion times may involve the use of auxiliary input data. In some embodiments, for example, the input heartbeat record may be accompanied by a record of activity of the subject measured using an activity monitor, such as an accelerometer.

In some embodiments, the knowledge base may comprise a template normal heart rate characteristic which may be obtained, for example, by averaging scaled and normalised heart rate characteristics of subjects in the training set who have been assessed by an expert assessor as having a normal, relatively healthy, mental state. The knowledge base may further comprise one or more template heart rate characteristics corresponding with other, e.g. abnormal or unhealthy, mental states which may be obtained, for example, by averaging scaled and normalised heart rate characteristics of subjects in the training set who have been assessed by an expert assessor as having such other mental states. In particular, the knowledge base may comprise a template depression heart rate characteristic obtained, for example, by averaging scaled and normalised heart rate characteristics of subjects in the training set who have been assessed by an expert assessor as having a depressed mental state.

In alternative embodiments, heart rate characteristics of subjects may be processed to compute a plurality of associated metrics. In some examples, four metrics are employed: a mean-awake heart rate; a ratio between mean-awake and -asleep heart rates; a slope of heart rate during the first half of the sleep period; and a slope of heart rate in the second half of the sleep period. As will be appreciated, these particular four metrics can be computed by fitting a piece-wise linear heart rate characteristic model to the received heartbeat record of a subject.

The knowledge base may comprise one or more data structures resulting from the application of machine learning algorithms to the metrics computed by processing the heart rate characteristics of subjects in the training set. Suitable machine learning algorithms include: decision tree learning; association rule learning; artificial neural networks; inductive logic programming; support vector machines; cluster analysis; Bayesian networks; reinforcement learning; representation learning; similarity learning; sparse dictionary learning; genetic algorithms; and/or other methodologies known to persons skilled in the art of machine learning.

In some embodiments, the knowledge base comprises data structures representing one or more classification trees, obtained by applying a decision tree learning algorithm over the metrics computed from the heart rate characteristics of subjects in the training set. As known to persons skilled in the art of machine learning, a number of decision tree algorithms are known, which may be suitable for this purpose, including: ID3 (Iterative Dichotomiser 3); C4.5; CART (Classification and Regression Tree); CHAID (Chi-square Automatic Interaction Detector); MARS; and conditional inference trees. A number of existing software applications provide implementations of one or more of the foregoing learning algorithms, including MATLAB and R.

In an embodiment, a decision tree learning algorithm is applied to generate two classification tree data structures, which are stored in the knowledge base. A first classification tree data structure classifies metrics computed from the heartbeat record of the subject into 'normal' or 'not normal'. A second classification tree data structure classifies the metrics computed from the heartbeat record of the subject into 'depressed' and 'not depressed'.

According to an embodiment, the method comprises classifying the subject as 'normal' or 'not normal' by executing the first classification tree and, in the event that the subject is classified as 'not normal', classifying the subject as 'depressed' or 'not depressed' by executing the second classification tree.

In another aspect, the invention provides a computer-implemented system for assessing a mental state of a subject, the system comprising:
  at least one microprocessor;
  at least one non-volatile storage device containing a knowledge base comprising data obtained via expert evaluation of a training set of subjects and embodying a computational model of a relationship between mental state and heart rate characteristics;
  at least one computer-readable memory device operatively associated with the microprocessor; and
  an input/output interface operatively associated with the microprocessor,
  wherein the memory device contains computer-executable instruction code which, when executed via the microprocessor, causes the microprocessor to effect a method comprising steps of:
    receiving, via the input/output interface, a heartbeat record of the subject, which comprises a sequence of heartbeat data samples obtained over a timespan which includes a pre-sleep period, a sleep period having a sleep onset time and a sleep conclusion time, and a post-sleep period;
    identifying, within the heartbeat record, at least the sleep onset time and the sleep conclusion time;
    using information in the knowledge base, applying the computational model to compute at least one metric associated with the mental state of the subject, and to generate an indication of mental state based upon the metric; and
    providing, via the input/output interface, the indication of the mental state of the subject.

The input/output interface may be a network interface providing access to a wide area network, such as the Internet.

In some embodiments of the invention, the heartbeat record of the subject may be obtained via a heart rate monitor device worn by the subject during the timespan including the pre-sleep period, the sleep period and the post-sleep period. The heartbeat monitor may comprise a wireless interface, such as a Bluetooth interface, for communication with a network-connected device, such as a smartphone, a tablet computer, a notebook computer, or a desktop computer. Alternatively, or additionally, the heart rate monitor device may comprise a wired interface, such as a USB interface, for connection to a network-connected device. A heartbeat record obtained via the heart rate monitor device may be transferred continuously (i.e. in real time) to another device. Alternatively, the heartbeat record, or a portion thereof, may be stored within the heart rate monitor device and data may be transferred periodically, upon completion of recording, or at a later time, e.g. upon connection to a network or suitable network-connected device.

An application may be provided for execution on the network-connected device to assist the subject in performing a measurement of a heartbeat record. Assistance may include providing the subject with instructions for fitting the heart rate monitor device, as well as for transferring measured heart rate data from the heart rate monitor device to the network-connected device.

The heartbeat record of the subject may be transferred from the network-connected device to the mental state assessment system via the wide area network, e.g. the Internet.

Further features and benefits of the invention will be apparent from the following description of embodiments, which is provided by way of example only and should not be taken to limit the scope of the invention as it is defined in any of the preceding statements, or in the claims appended hereto.

BRIEF DESCRIPTION OF THE DRAWINGS

Embodiments of the invention will now be described with reference to the accompanying drawings in which like reference numerals indicate like features, and wherein.

DETAILED DESCRIPTION OF EMBODIMENTS

Figure 1:
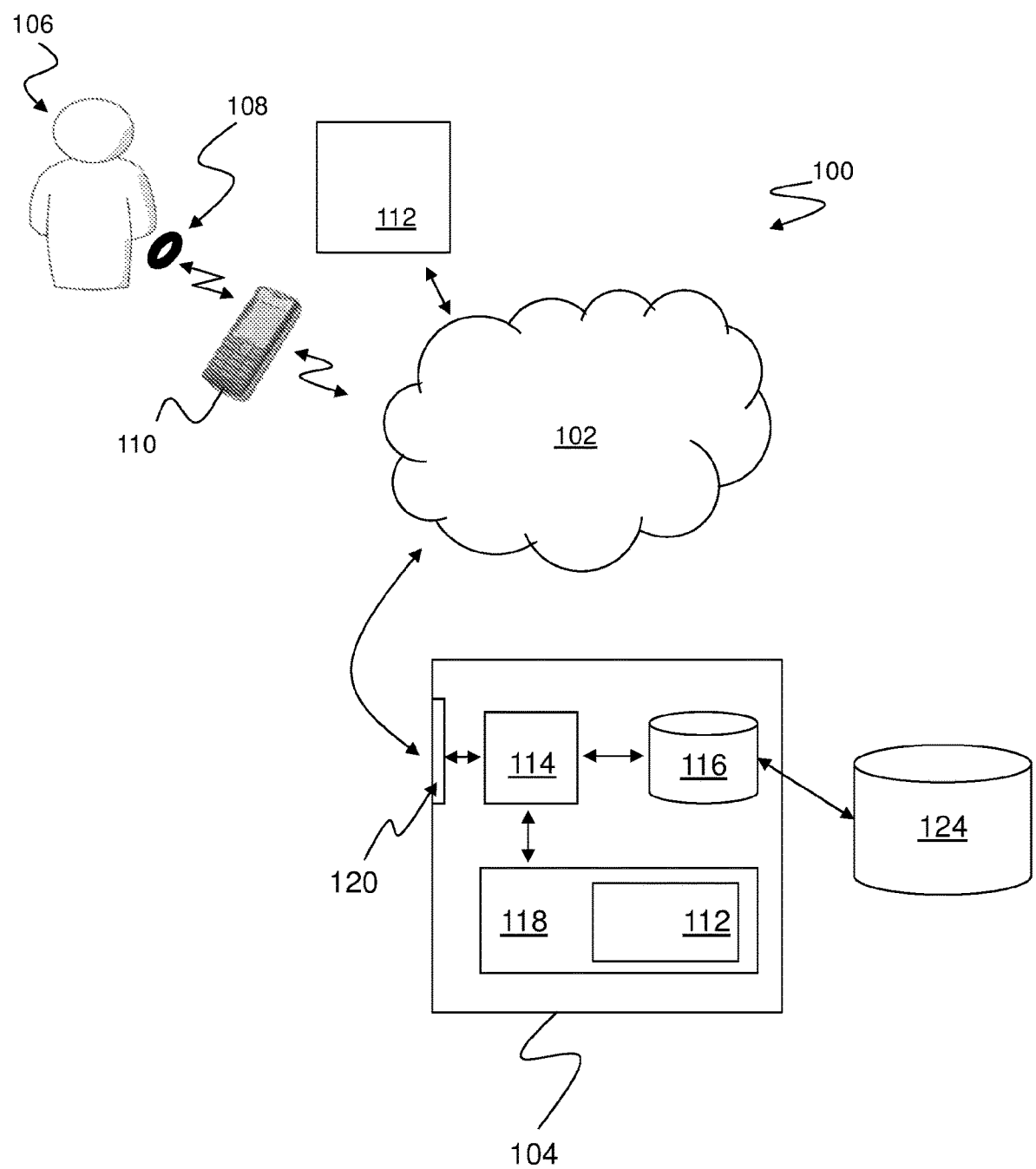
FIG. 1 is a schematic diagram illustrating a system for assessing mental state of a subject, embodying the invention.

FIG. 1 is a block diagram illustrating an online system 100 embodying the invention. The system 100 employs a wide area communications network 102, typically being the Internet, for messaging between different components of the system, each of which generally comprises one or more computing devices.

The system 100 includes an assessment platform 104 and an assessment subject 106 who is, in this example, located remotely from the assessment platform 104. The subject 106 is provided with a heart rate monitor 108, which may be capable of communications with one or more portable devices, such as smartphone 110, and/or one or more desktop devices such as a personal computer 112. Communications between the heart rate monitor 108 and smartphone 110 are preferably via a wireless communications channel, such as Bluetooth. Other types of communications channel suitable for transfer of data between the heart rate monitor 108 and devices 110, 112 include Wi-Fi, wired Ethernet, and other forms of wired connections, such as USB.

In some embodiments, such as those described herein, heart rate data collected by the heart rate monitor 108 is transferred to another user device, such as smartphone 110 or desktop PC 112, and then transferred to the assessment platform 104. However, in other embodiments of the invention a smart heart rate monitor 108 may include a network interface, such as a Wi-Fi interface or a cellular mobile interface including, e.g., a Nano Sim card, enabling it to connect and transfer data directly to the assessment platform 104 via the Internet 102. Alternatively, the heart rate monitor 108 may be integrated with a cloud-based platform, such as a healthcare platform, e.g. Philips Healthsuite, or other cloud platform, e.g. Samsung SAMIIO, for upload of data to the cloud for retrieval by the assessment platform 104. In still further embodiments, the functionality of the assessment platform 104 may be provided at the location of the assessment subject 106, such as via software made available for installation on the subject PC 112. In yet another alternative, the assessment platform 104 may be provided at the location (e.g. surgery or office) of a health care professional who is monitoring the mental health of the subject 106. Other combinations and variations of the above arrangements are also possible, within the scope of the invention, such as the collection of heart rate data by the monitor 108 for transfer to a portable or desktop device of a health care professional, and subsequent submission for processing by a remotely located assessment platform 104. It should therefore be appreciated that the exemplary architecture of the system 100 is not the only configuration in which the invention may be implemented.

Turning now to the assessment platform 104, it may generally comprise one or more computers, each of which includes at least one microprocessor 114. The number of computers and processors 114 will generally depend upon the required processing capacity of the system, which in turn depends upon the anticipated workload, i.e. the number of assessment subjects 106 having access to the platform 104, and the volumes of data to be processed. In some embodiments, a third-party cloud-computing platform may be employed for the platform 104, thereby enabling the physical hardware resources to be allocated, and changed, dynamically in response to demand. However, for simplicity in the remainder of the description, it is assumed that the exemplary assessment platform 104 includes a single computer with a single microprocessor 114.

The microprocessor 114 is interfaced to, or otherwise operably associated with, a non-volatile memory/storage device 116. The non-volatile storage 116 may be a hard disk drive, and/or may include a solid-state non-volatile memory, such as read only memory (ROM), flash memory, or the like. The microprocessor 114 is also interfaced to volatile storage 118, such as random access memory (RAM) which contains program instructions and transient data relating to the operation of the platform 104. In a conventional configuration, the storage device 116 may contain operating system programs and data, as well as other executable application software necessary to the intended functions of the assessment platform 104. In the embodiments shown, the storage device 116 also contains program instructions which, when executed by the processor 114, enable the assessment platform 104 to perform operations relating to the implementation of a mental state assessment method, and more particularly a method of assessing stress levels of the subject 106, embodying the invention. In operation, instructions and data held on the storage device 116 are transferred to volatile memory 118 for execution on demand.

The microprocessor 114 is also operably associated with a network interface 120 in a conventional manner. The network interface 120 facilitates access to one or more data communications networks, such as the Internet 102, employed for communication between the platform 104 and subject devices, e.g. 110, 112.

In use, the volatile storage 118 includes a corresponding body 122 of program instructions configured to perform processing and operations embodying features of the present invention, comprising various steps in the processes described below with reference to the flowcharts, data structures, and software architectures illustrated in FIGS. 3 to 8.

Furthermore, in the presently described embodiment, the program instructions 122 include instructions implementing communications with one or more client applications, such as an application executing on a smartphone 110, desktop PC 112, or other device operated by the subject 106 or a supervising health care professional. These communications operations enable heartbeat records of the subject 106, recorded using the heart rate monitor 108, to be received for processing by the assessment platform 104.

The program instructions 122 may further include instructions embodying a web server application. Data stored in the non-volatile 116 and volatile 118 storage may then include web-based code for presentation and/or execution on subject devices (e.g. HTML or JavaScript) facilitating a web-based interface to the assessment platform. The web-based interface may, for example, enable upload of heartbeat record data from any device, including smartphone 110 or desktop PC 112, to the assessment platform 104. The web interface may also enable the subject 106 and/or their supervising health care professional, via devices 110 and/or 112, to access data that has been stored and processed by the assessment platform 104.

The system 100 also includes a knowledge base 124, which contains information generated via machine learning methodologies, using data obtained via expert evaluation of one or more training sets of subjects, and embodying a computational model of a relationship between mental state, e.g. subject mental health, and heart rate characteristics.

Various machine-learning methodologies may be employed in different embodiments of the invention, including: decision tree learning; association rule learning; artificial neural networks; inductive logic programming; support vector machines; cluster analysis; Bayesian networks; reinforcement learning; representation learning; similarity learning; sparse dictionary learning; and/or genetic algorithms.

Embodiments described herein, particularly with reference to FIGS. 4 to 8, employ techniques including metric learning and decision tree learning. However, these approaches should be regarded as illustrative only, and do not exclude the use of other learning techniques and computational models from the scope of the invention.

The knowledge base 124 may be contained within the non-volatile storage 116, or may be stored in a separate storage device, which may be directly connected to the assessment platform 104, or may be remotely located. In particular, since the knowledge base 124 may ultimately grow to contain very large amounts of training and historical subject data, it may be advantageous for the knowledge base 124 to be stored in a large data centre and/or one or more distributed databases, e.g. in a cloud storage service. The exact form and location of the knowledge base 124 is not critical, so long as the required data, as described below, is accessible for processing by the assessment platform 104.

Figure 2A:
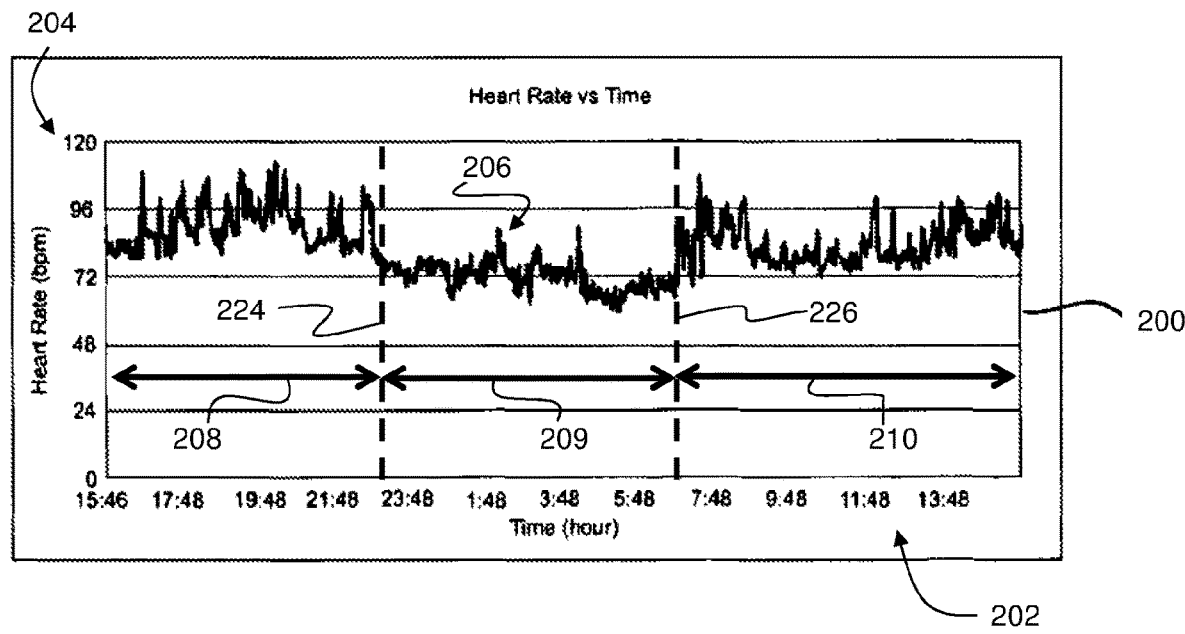
FIG. 2 shows graphs of exemplary heart rate and activity records embodying the invention.
Figure 2B:
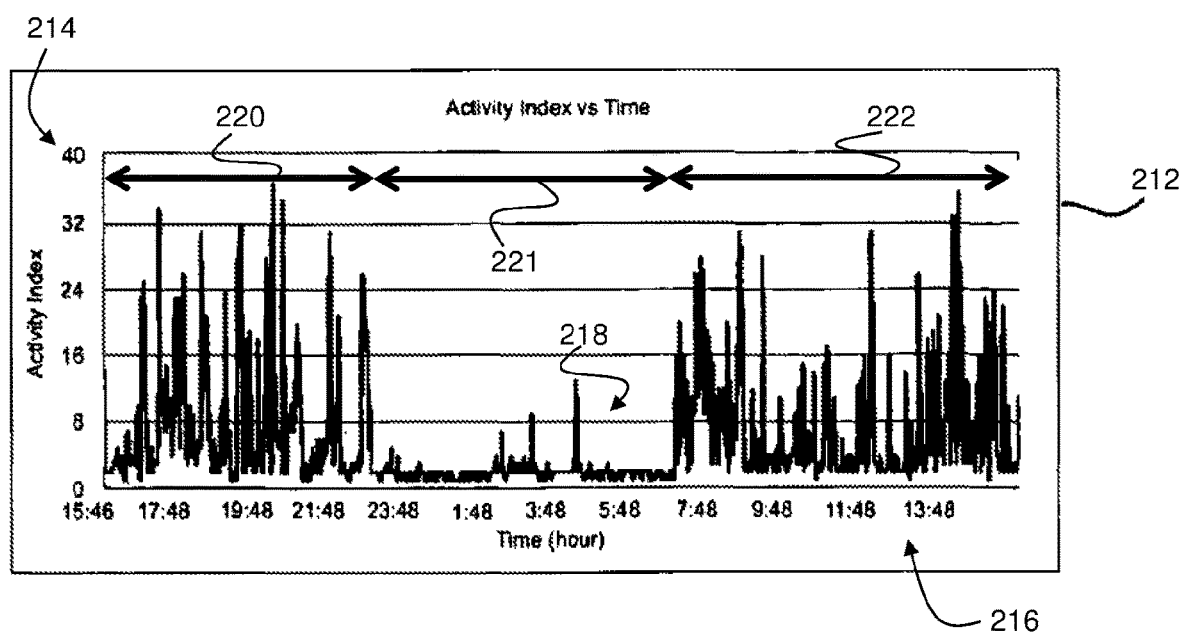

Turning now to FIG. 2(*a*), there is shown a graph 200 of an exemplary heartbeat record of a subject 106. Time is shown on the horizontal axis 202, and minute-averaged heart rate in beats per minute, on the vertical axis 204. Accordingly, the heartbeat record of the subject represented by the graph 200 comprises a sequence of heartbeat data samples, obtained and recorded at a rate of one per minute over the total timespan illustrated on the horizontal axis 202. In this particular example, the record covers a full 24-hour period, however embodiments of the invention may require only a portion of the full record 206, comprising a pre-sleep period 208, a sleep period 209, and a post-sleep period 210.

In some embodiments, the pre-sleep 208, sleep 209 and post-sleep 210 periods may be automatically identified. One technique for automatic identification of the sleep period 209 is through the use of an activity monitor, such as an accelerometer which may be incorporated into the heart rate monitor 108, or into another wearable device worn by the subject 106. FIG. 2(*b*) shows a graph 212 of subject activity obtained using such an activity monitor, and corresponding with the heartbeat record of FIG. 2(*a*). The horizontal axis 214 shows time, while the vertical axis 216 is an activity index, which is computed based upon the level of activity detected by the activity monitor during each minute of the recording period. The trace 218 of the activity record shows three very distinct periods, i.e. a first waking period 220 of relatively high activity, a sleep period 221 in which there is little or no activity, and a further waking period 222 of high activity.

The extremely distinct transitions between periods 220, 222, of high activity, and period 221 of low activity, enables relatively simple and accurate extraction of a sleep onset time 224 and a sleep conclusion time 226, separating the pre-sleep 208, sleep 209, and post-sleep 210 periods.

While activity levels provide one mechanism to identify the sleep onset 224 and sleep conclusion 226 times, other methods may be used in alternative embodiments. For example, it is also apparent from the graph 200 that the sleep period 209 corresponds with a general reduction in heart rate. Accordingly, suitable processing of the heartbeat record 206 may be employed to assist in identifying the sleep onset 224 and sleep conclusion 226 times. Additionally, or alternatively, the subject 106 may provide an estimate of sleep and waking times in order to assist in the detection of sleep onset 224 and conclusion 226. It will therefore be appreciated that various techniques to identify these transition times with sufficient accuracy and reliability are available for use in different embodiments of the invention.

Figure 3:
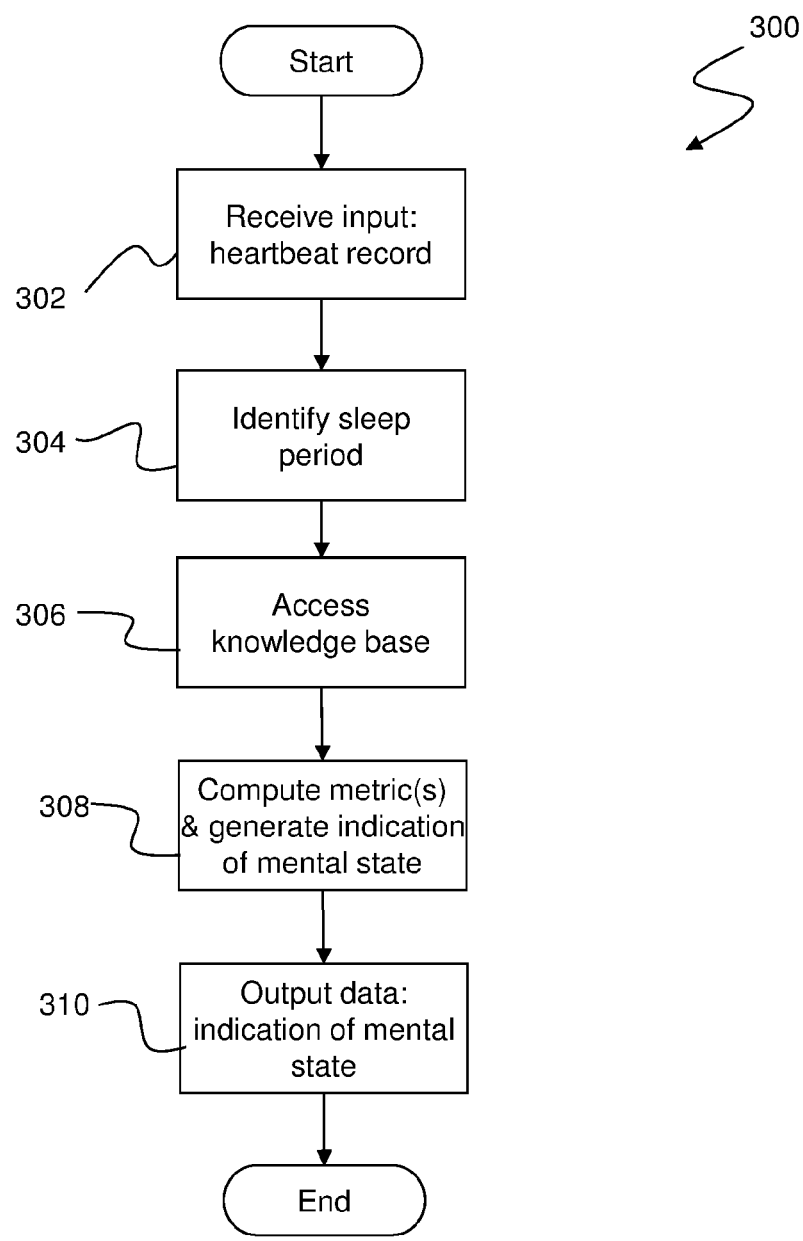
FIG. 3 shows a flowchart of a method of assessing a mental state embodying the invention.

FIG. 3 is a flowchart 300 showing a method of assessing a mental state, e.g. mental health, of the subject 106, according to an embodiment of the invention. Firstly, at step 302, a heartbeat record of the subject is received as input. In initial processing 304, the sleep period 209, having sleep onset time 224 and sleep conclusion time 226, is identified.

The assessment method 300, which may be implemented via suitable program instructions executed by the processor 114 of the assessment platform 104, then proceeds to further analyse the heartbeat record in order to perform an assessment of the subject's stress levels. In order to do this, information in the knowledge base is accessed 306. Exemplary contents of the knowledge base are described below with reference to FIGS. 5(a) to 5(c), while corresponding exemplary training methods for constructing the knowledge base are described with reference to FIGS. 7 and 8. For present purposes it is sufficient to note that the information accessed in the knowledge base is based upon expert evaluation of a training set of subjects, and is constructed so as to enable the assessment platform 104 to estimate the mental state of the subject 106 based upon the knowledge base contents. Generally, this involves a process 308 of computing one or more metrics associated with the mental state of the subject 106, and generating an indication of the mental state based upon those metrics.

At step 310 a resulting indication of mental state, e.g. a mental health indication, is output. The output result may be stored in a subject record within the non-volatile storage 116, in the knowledge base 124, or in some other database. Alternatively, or additionally, the resulting indication may be presented to the subject and/or to a supervising health care professional, for example via a web interface, or via an application interface, using software executing on a connected device, such as the smartphone 110 or desktop PC 112.

Figures 4A, 4B:
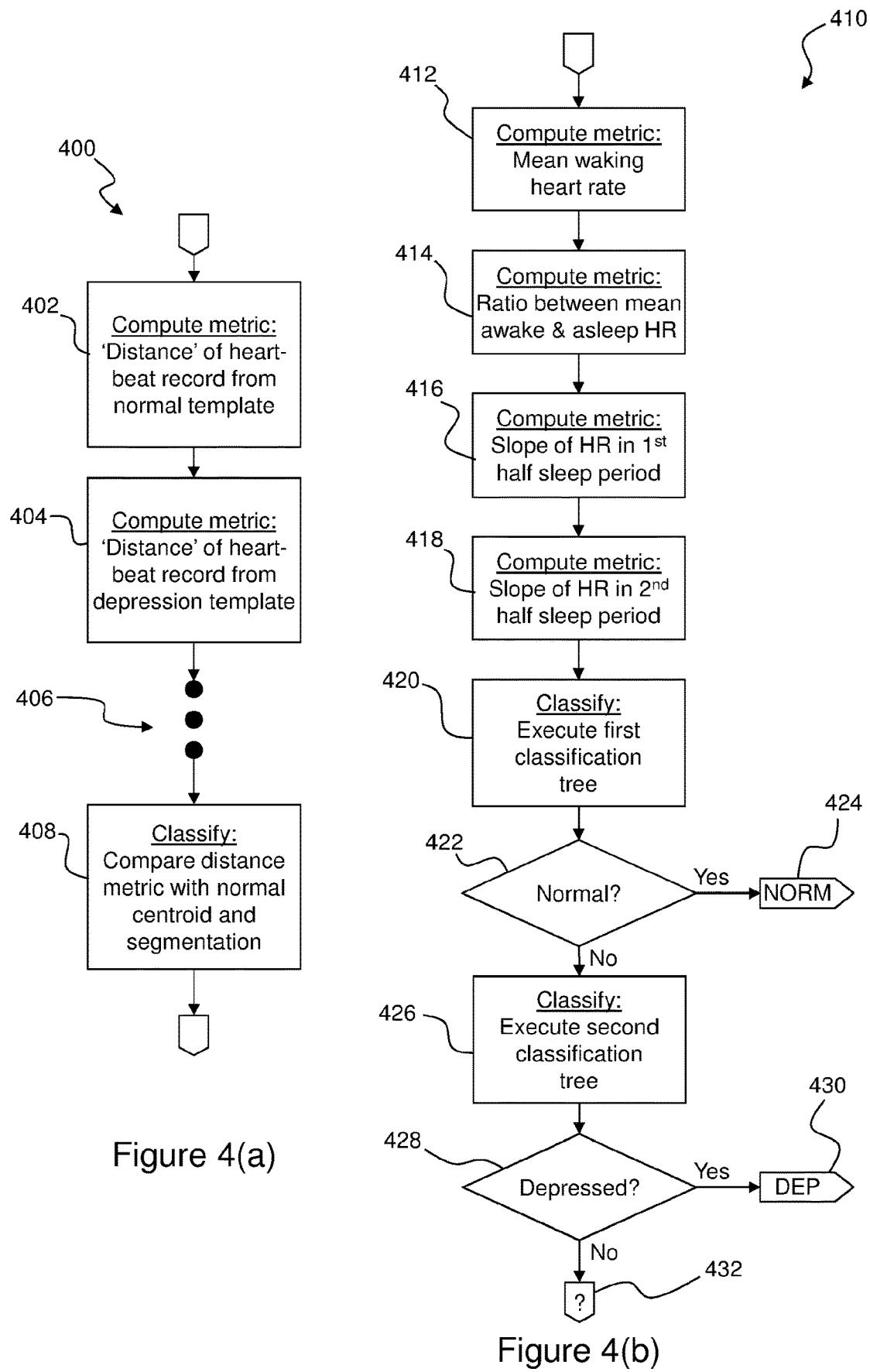
FIGS. 4(a) and 4(b) are flowcharts corresponding with two alternative computational models embodying the invention.
Figure 5A:
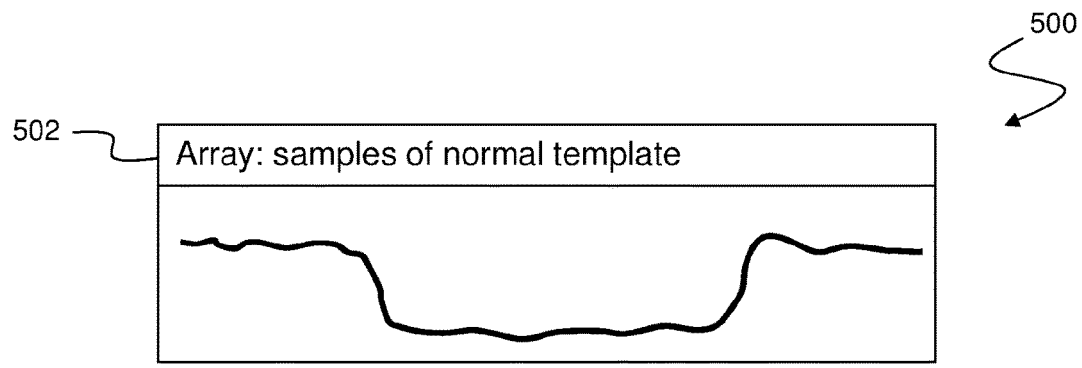
FIGS. 5(a)-5(c) are block diagrams illustrating the content of a knowledge base corresponding with the computational model of FIG. 4(a)
Figure 5B:
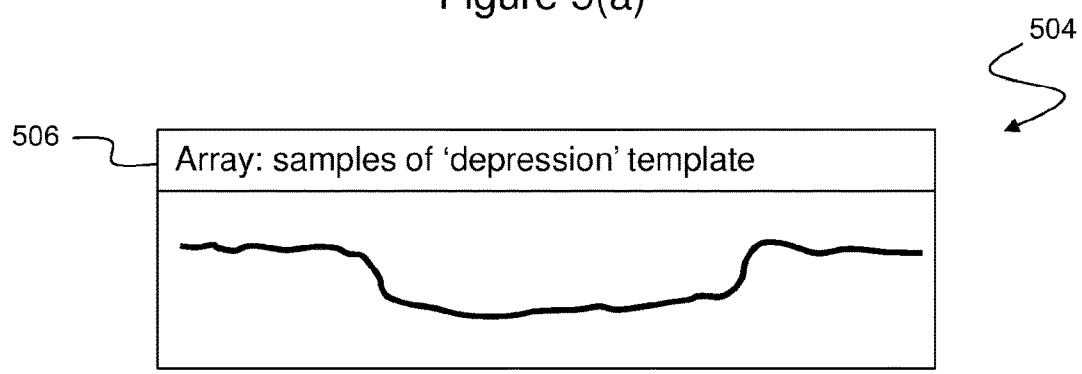
Figure 5C:
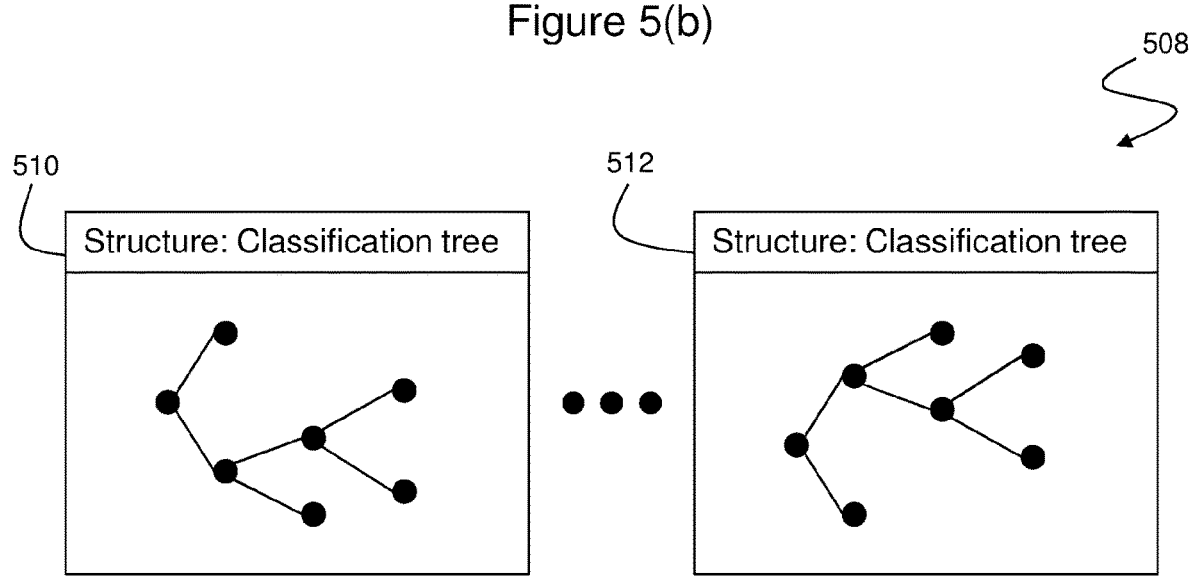

FIGS. 4(a) and 4(b) are flowcharts corresponding with two alternative computational models embodying the invention. FIGS. 5(a) to 5(c) are block diagrams illustrating contents of the knowledge base for these models.

According to a first model, herein termed the 'template model', a process of computing metrics and generating an indication of subject mental state is represented by the flowchart 400, and the knowledge base contents 500, 504. More particularly, the knowledge base 124 contains content 500 which includes a 'normal template' 502. The normal template 502 is a representative record corresponding with a patient without any significant mental health issues. The knowledge base 124 further contains content 504 which includes a 'depression template' 506. The depression template 506 is a representative record corresponding with a subject clinically diagnosed with depression. The way in which the normal template 502 and the depression template 506 are obtained will be described in greater detail below with reference to FIG. 7(a).

Returning to FIG. 4(a), in step 402 a metric is computed for the assessment subject 106, which comprises a measure of difference between the heartbeat record of the subject, and the normal template 502. At step 404, a second metric is computed for the assessment subject 106, which comprises a measure of difference between the heartbeat record of the subject, and the depression template 506. In other embodiments of the invention, templates may be generated corresponding with other mental health conditions, such as anxiety, panic disorder, OCD, schizophrenia, and so forth. If such templates exist, similar measures of difference are computed, comprising further metrics corresponding with each template, as indicated by the ellipsis 406. A suitable measure of difference may be, for example, a mean squared difference between the subject heartbeat record and the template in each case. The difference may be computed over the entirety of the subject heartbeat record, or over only a selected portion of the heartbeat record. In particular, the difference may be computed for the portion of the subject heartbeat record corresponding with the sleep period, i.e. between the sleep onset time, and the sleep conclusion time.

At step 408, the mental state of the subject 106 is classified by comparing the difference metrics computed at step 402 and step 404 (and, if available, any further difference metrics computed at steps 406), with the smallest value determining the indication of mental state of the subject 106.

The flowchart 410, and corresponding knowledge base content 508, exemplify a class of multi-parametric computational models. The multi-parametric models described herein employ four metrics that are computed from the input heart rate record of the subject 106. These four metrics are:
the mean awake heart rate, i.e. the average heart rate during the pre-sleep 208 and post-sleep 210 periods;
the ratio of heart rates, computed as a ratio between the average waking heart rate, and the average heart rate during the sleep period 209;
a first slope metric, being a measure of the slope (i.e. change as a function of time) of the subject's heart rate during the first half of the sleep period 209; and
a second slope metric, being a measure of the slope of the heart rate in the second half of the sleep period 209.

As will be appreciated, these four parameters fully define a piecewise-linear representation of the patient heartbeat record, having a constant waking heart rate value and a sleeping heart rate value that changes in accordance with the first slope metric during the first half of the sleep period 209, and in accordance with the second slope metric during the second half of the sleep period 209. The inventors have found this particular parameterisation of the heartbeat record to provide an effective basis for machine learning and prediction of mental state, with the assistance of expert assessment of subjects in a training set.

Accordingly, at steps 412, 414, 416 and 418 the four metrics described above are computed.

According to an exemplary multi-parametric computational model, the knowledge base 124 contains content 508 which comprises one or more data structures, e.g. 510, 512. In the presently disclosed embodiment, these data structures represent classification trees. A first classification tree 510 is constructed to classify the subject 106, based upon the four computed metrics discussed above, as 'normal' or 'not normal'. A second classification tree 512 is constructed to classify the subject 106, based upon the four metrics, as 'depressed' or 'not depressed'. The way in which the classification trees 510, 512 are constructed will be described in greater detail below with reference to FIG. 7(b).

Returning to FIG. 4(b), at step 420 the metrics computed for the subject 106 are run through the first classification tree 510 at step 420. The output is checked at step 422, and if the subject 106 is classified as normal the process terminates at 424, with a corresponding 'normal' indication. Otherwise, the second classification tree is run at step 426. The output is checked at step 428, and if the subject 106 is classified as depressed then the process terminates with an indication of 'depressed' at 430. Otherwise, an indication of neither normal nor depressed is returned 432.

In all cases, the next steps, in terms of diagnosis and treatment of the subject 106, will occur in conjunction with a health care practitioner. For example, a test in accordance with an embodiment of the invention may be ordered by the subject's local doctor or general practitioner. If the resulting indication is 'normal', then the practitioner may determine that no further action is necessary, or may order further tests of a similar or different nature. However, in the event that an indication of depression, or otherwise abnormal mental state, is obtained, then the practitioner may determine that some intervention is appropriate, such as treatment and/or referral to a specialist, such as a psychologist or psychiatrist, for further diagnosis and treatment.

Figure 6:
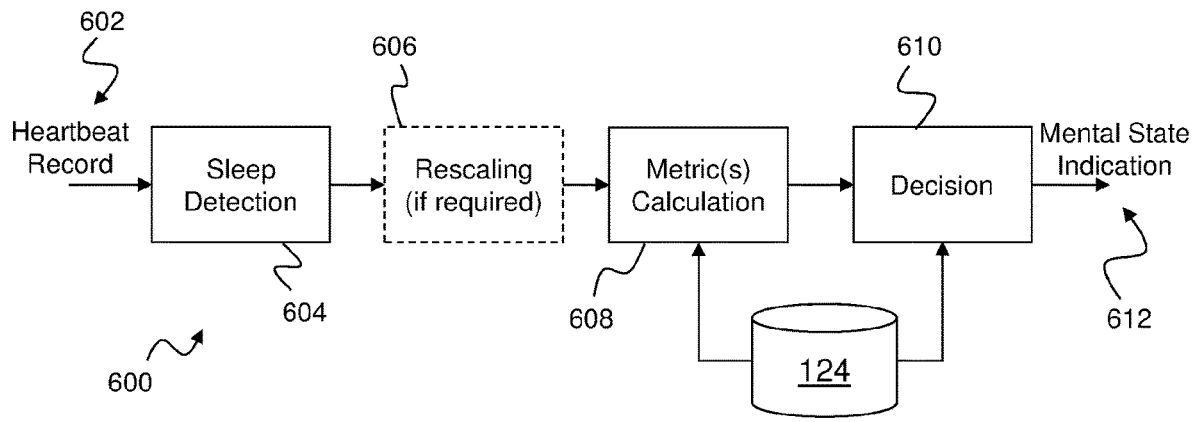
FIG. 6 is a block diagram illustrating the main software processing components of a computer implementation of embodiments of the invention.

Turning now to FIG. 6, there is shown a block diagram 600 illustrating the main software processing components of a computer implementation embodying the invention. The input heartbeat record data 602 is processed by sleep detection module 604, in order to identify the sleep onset and conclusion times. The record is optionally further processed by a rescaling module 606. The rescaling module processes the input data 602 in order to obtain a rescaled record, wherein the heart rate values have been normalised between zero and one, and the time adjusted to a standard scale, e.g. zero to 1,000 time units. Of the embodiments described in detail above, the rescaling is employed in the template model, in which it is important to ensure similarity among all of the heartbeat records that are being compared against the normal template 502, the depression template 506, and/or any other templates contained within the knowledge base 124. Rescaling is not required for the multi-parametric model described above, although it may be used in the computation of other metrics in accordance with alternative embodiments of the invention.

Metric calculation module 608 computes the relevant metric, or metrics, associated with the particular computational model used in an embodiment of the invention. For example, in the template model the metric calculation module 608 computes a first value representing the difference between the heartbeat record of the subject 106 and the normal template 502, and a second value representing the difference between the heartbeat record of the subject 106 and the depression template 506. In the multi-parametric models, the metric calculation module 608 computes the four metrics described above, with reference to FIG. 4(b).

In some embodiments, in order to compute the metric, or metrics, the metric calculation module 608 accesses the knowledge base 124. For example, in the template model, the metric calculation module 608 retrieves the normal template 502 and the depression template 506 from the knowledge base 124.

The decision module 610 classifies the mental state of the subject 106 according to the rules associated with the particular computational model. For example, in the template model the decision module 610 classifies the mental state of the subject 106 by comparing the first and second distance values, corresponding with the normal and depression templates, to determine which template is most similar to the heart beat pattern of the subject 106.

In the classification tree model, the decision module 610 classifies the mental state of the subject 106 by executing the one or more classification trees stored in the knowledge base 124.

Typically, the decision module 610 requires access to the knowledge base 124, in order to retrieve the decision criteria. An output mental state indication 612 is produced from the decision module 610.

Figure 7A:
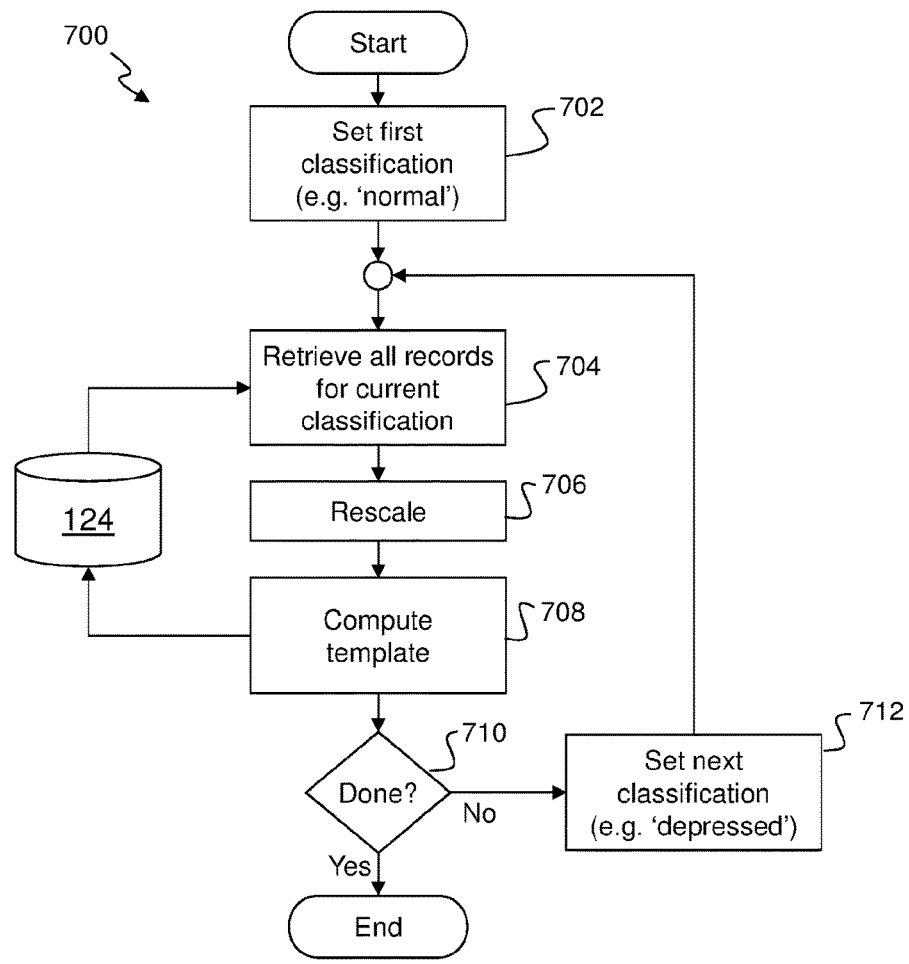
FIG. 7(a) is a flowchart of a knowledge base construction method corresponding with the computational model of FIG. 4(a)
Figure 7B:
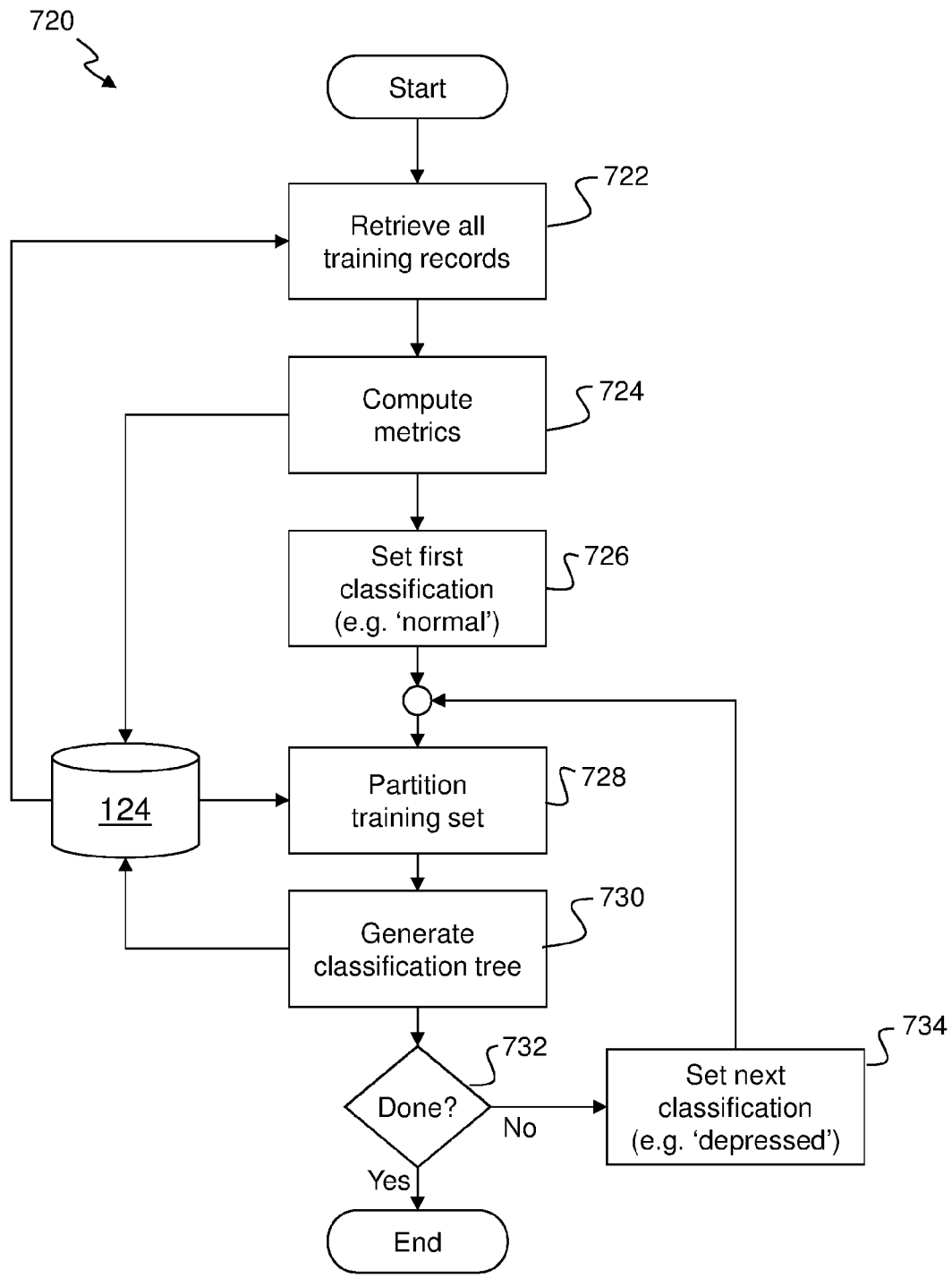
FIG. 7(b) is a flowchart of a knowledge base construction method corresponding with the computational model of FIG. 4(b)

FIG. 7 shows a flowchart 700 corresponding with the algorithm for knowledge base construction according to the template model. For this algorithm, and for the multi-parametric classification tree algorithm discussed below with reference to FIGS. 7(b) and 7(c), a precondition is that the knowledge base 124 includes a data set of training records. Each training record comprises a heartbeat record of a test subject, along with an associated diagnosis/assessment performed by an expert, such as a trained medical practitioner. The assessment may be conducted based upon the expert's review of the test subject heart rate records or may be obtained by other diagnostic means, such as interviews between each test subject and the expert assessor. It is these actual assessments associated with the data in the training set that provide the primary expert knowledge within the knowledge base. This information is then used to build computational models embodying this expert knowledge, which can then be used to generate an indication of the possible mental state of a subsequent unseen subject 106, based upon an input heartbeat record of the subject.

Returning to the template model training algorithm 700, at step 702 a first classification for training is set. This classification is selected from one of the available diagnoses performed by the expert clinician and associated with a subset of the training records in the knowledge base 124. Accordingly, for example, the first classification selected at step 702 may be 'normal'.

At step 704 all of the records from the training set having the first classification (e.g. 'normal') are retrieved. Each record comprises a sequence of heartbeat data samples, such as those illustrated in the graph of FIG. 2(a). At step 706 the retrieved data records are rescaled, such that heart rate is normalised between zero and one, and sleep period durations are normalised to a common timescale. At step 706, an average of all of the retrieved and rescaled test subject records is computed. This is a sample-by-sample averaging process, which results in the generation of a single representative heartbeat record, i.e. the template. In this example, the initial template is thus the normal template 502, which is then stored in the knowledge base 124.

At step 710 a check is performed to determine whether there are further classifications for which templates are required. In the exemplary embodiment, at least one further template is generated, corresponding with subjects within the training set who have been assessed as suffering from depression. Accordingly, at step 712 the classification is set to 'depression', and the retrieval 704, rescaling 706, and template computation 708 steps are repeated.

The process of computing templates can be continued for all classifications for which expert clinician assessments or diagnoses exist within the training set.

FIG. 7(b) shows a flowchart 720 of a knowledge base construction method comprising construction of classification trees, and corresponding with the computational model 410 shown in FIG. 4(b). At step 722, training data records are retrieved from the knowledge base 124. The records retrieved at step 722 may comprise all of the records in the training set, or may comprise a selected subset.

At step 724, the set of four exemplary metrics (i.e. mean waking heart rate, heart rate ratio, first slope metric, and second slope metric) are computed for each one of the retrieved training data records. Accordingly, there is obtained from the training set a collection of records of the form:

$$(x;Y)=(x_1,x_2,x_3,x_4;Y)$$

In the above expression, the dependent variable Y represents the mental health state of each subject in the training set, as assessed by the expert clinician (e.g. 'normal', 'depression', etc), while the vector x is composed of the four metrics.

Given this data, at step 726 a first classification is selected, for example 'normal'. At step 728 the data records are partitioned such that each record is classified as falling within the classification set (i.e. having an assessment of 'normal'), or falling outside the classification set (i.e. any assessment other than 'normal', generically being 'not normal').

At step 730 a classification tree is constructed for distinguishing between 'normal' and 'not normal' within the training set, and accordingly for predicting membership of these complementary classifications in future unseen data. Any suitable known decision tree learning algorithm may be employed at step 730, including: ID3; C4.5; CART; CHAID; MARS; and/or conditional inference trees. Existing software tools including, though not limited to, MATLAB and R, or existing programming libraries, such as scikit-learn for the Python programming language, may be employed to implement the learning algorithm at step 730.

At step 732, a check is performed to determine whether there are further classifications for which classification trees must be generated. If so, then the next classification value is selected at step 734, and steps 728 and 730 are repeated. In the exemplary embodiment, a second classification tree is generated for distinguishing between 'depression' and 'not depression'.

Figure 8A:
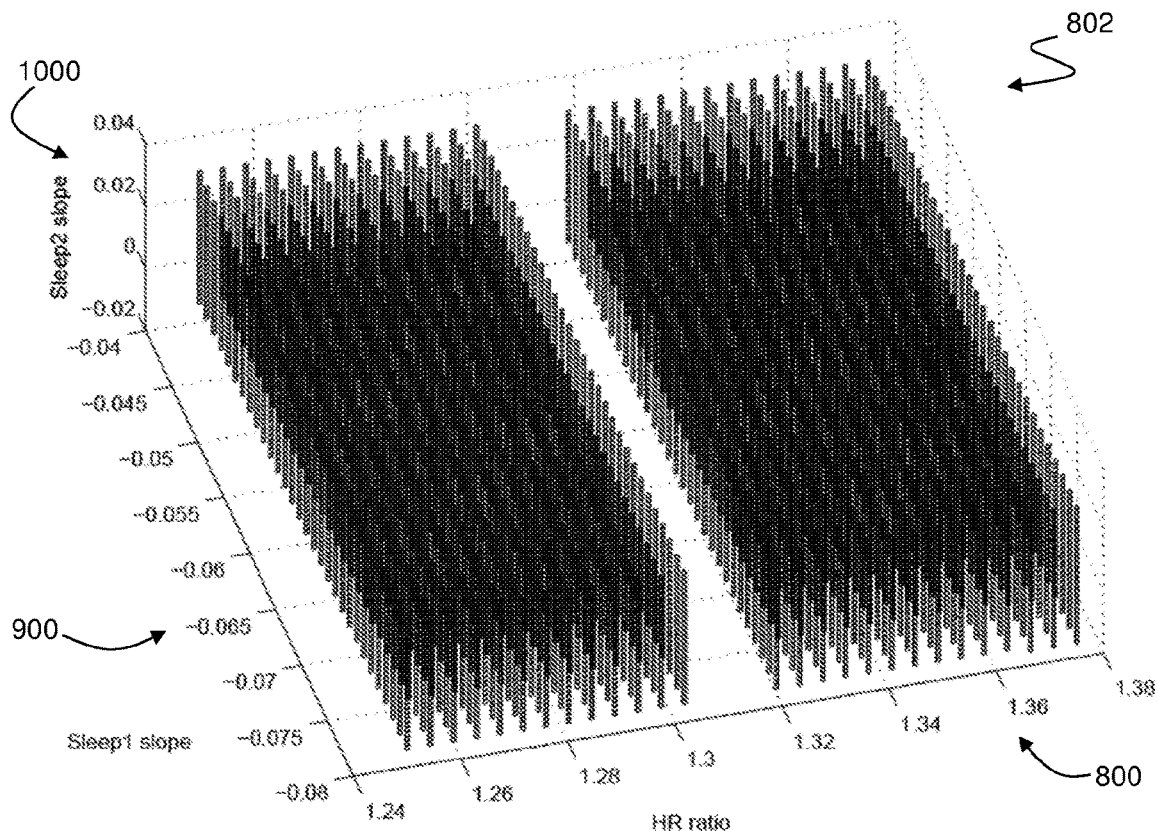
FIGS. 8(a) and 8(b) show three-dimensional chart representations of segmentation of subjects in a training set having an average waking heart rate of around 80 beats per minute.
Figure 8B:
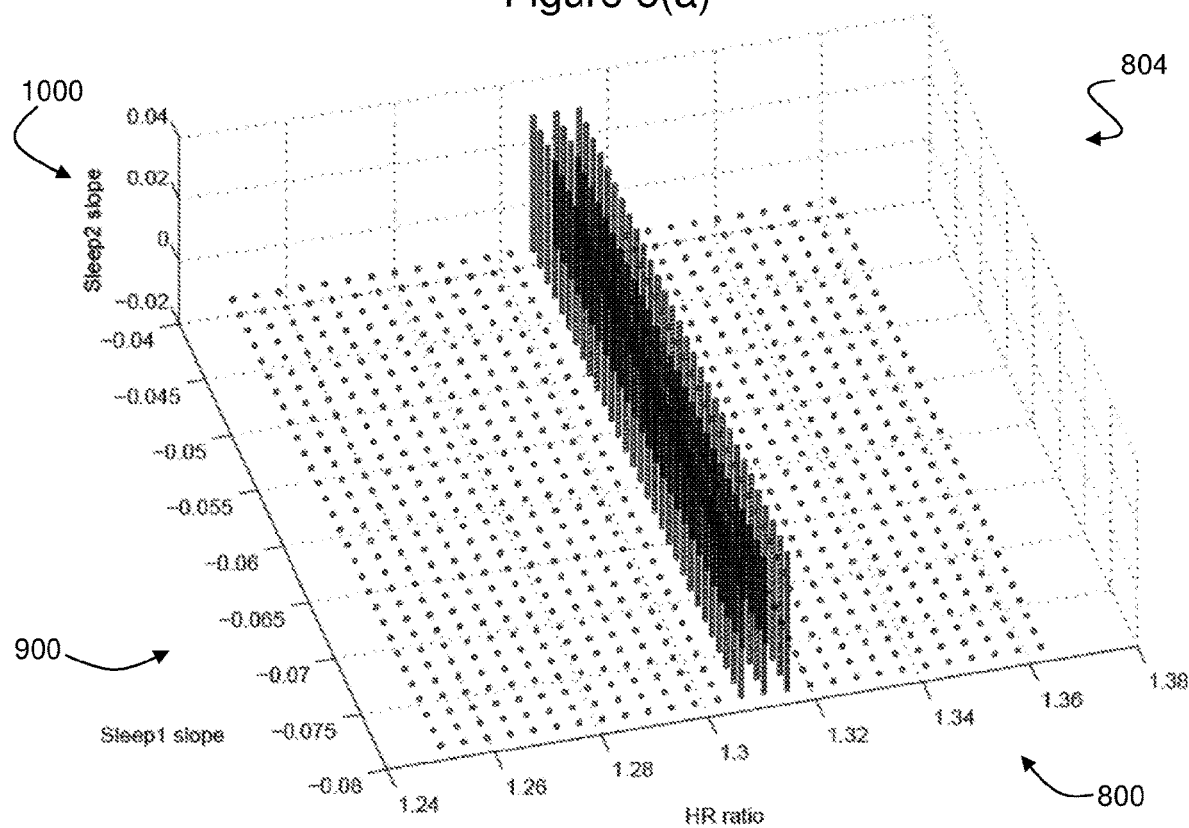
Figure 9A:
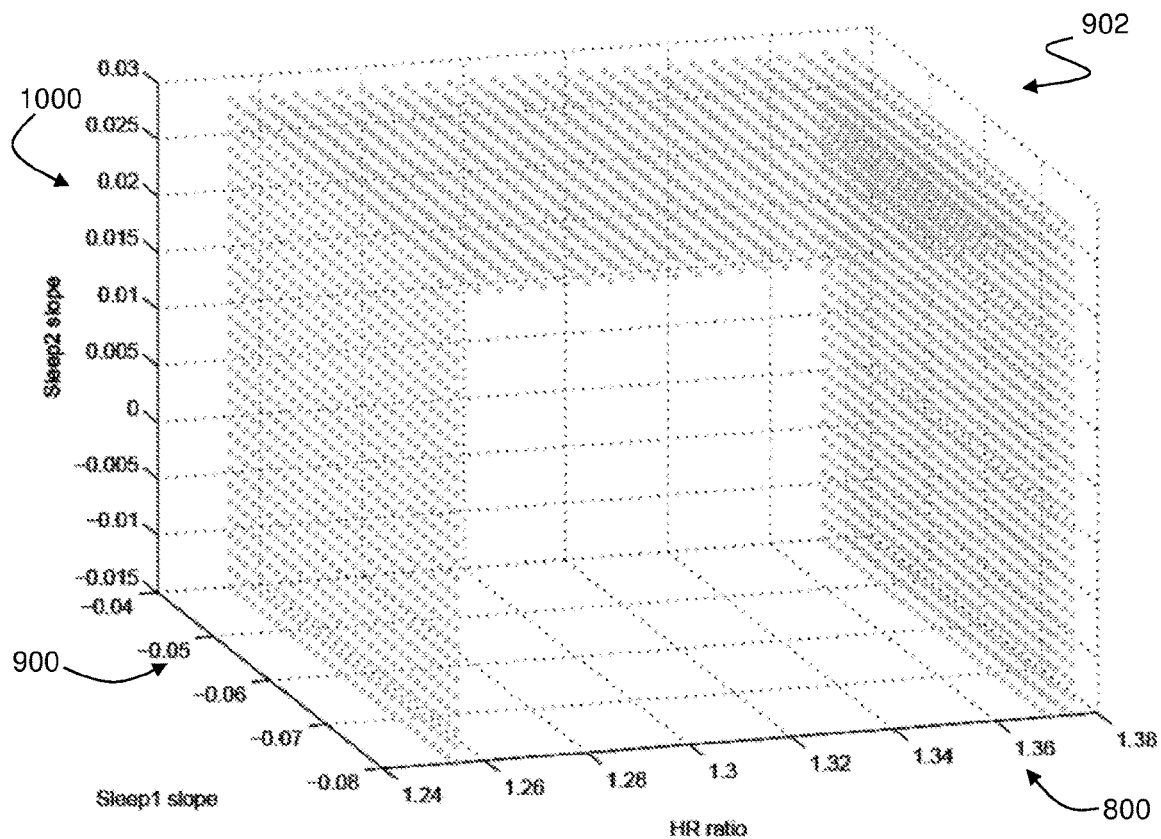
FIGS. 9(a) and 9(b) show three-dimensional chart representations of segmentation of subjects in a training set having an average awake heart rate of around 87.7 beats per minute.
Figure 9B:
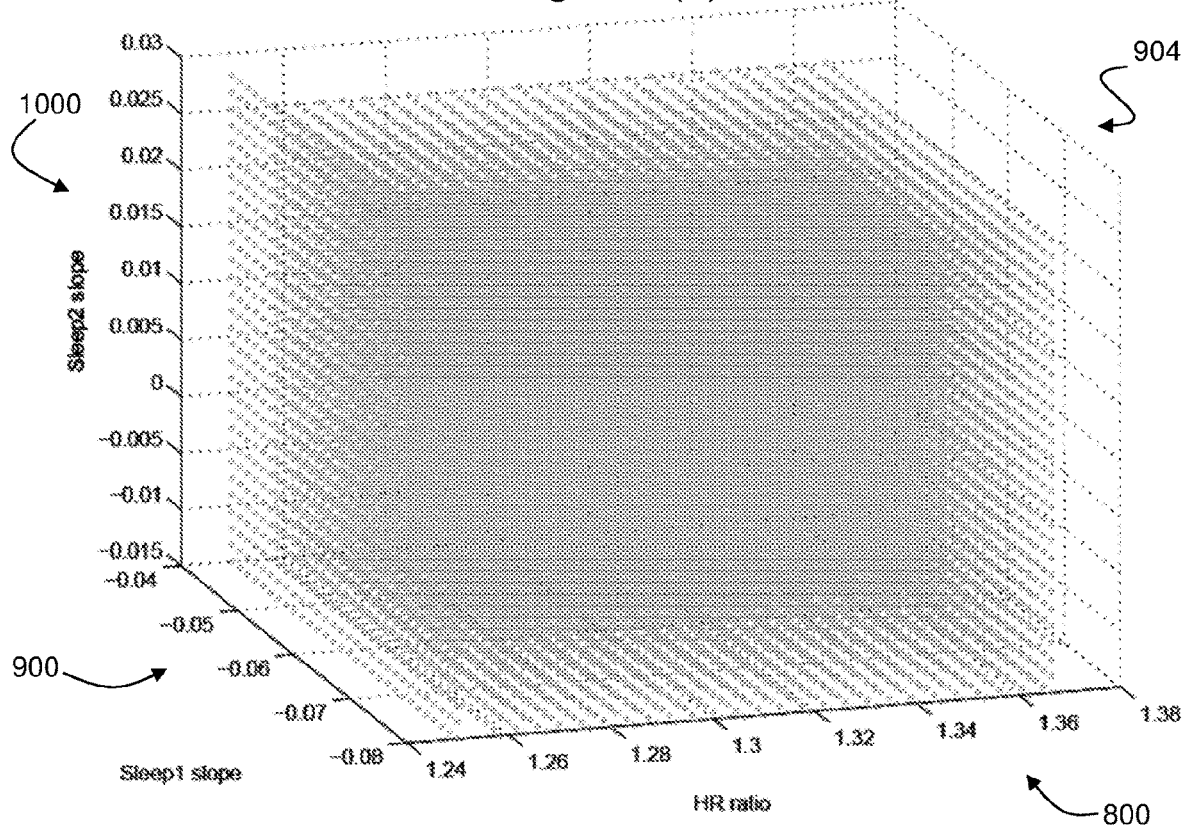
Figure 10A:
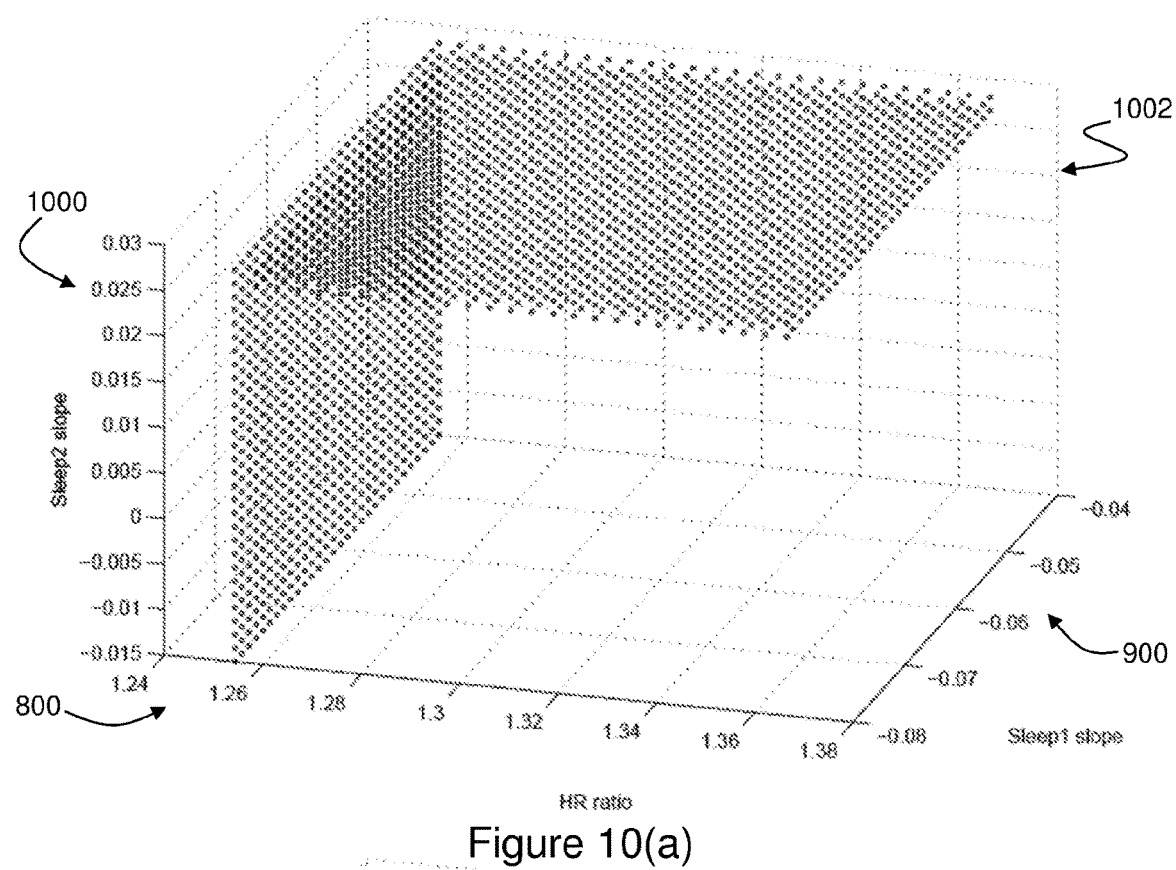
FIGS. 10(a) and 10(b) show three-dimensional chart representations of segmentation of subjects in a training set having an average waking heart rate of around 96 beats per minute.
Figure 10B:
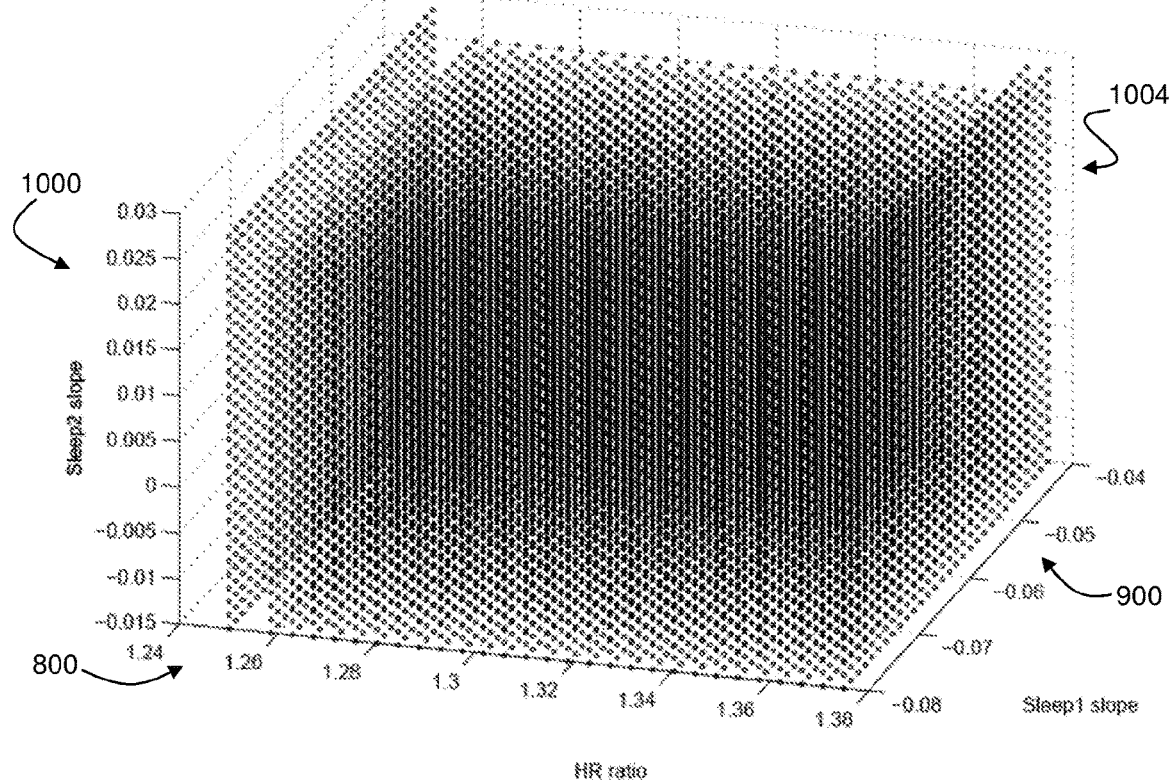

By way of illustration of the effectiveness of the classification tree algorithms employed in an embodiment of the invention, FIGS. 8 to 10 show a number of three-dimensional chart representations for segmentations of subjects in a training set between 'normal' and 'not normal'. Each chart has axis representing three of the four metrics, namely the heart rate ratio 800, the first slope metric 900 and the second slope metric 1000. The fourth metric, namely waking heart rate, is different for each of FIGS. 8, 9 and 10, i.e. each represents one slice through the four-dimensional space defined by the four metrics. In particular, FIGS. 8(*a*) and 8(*b*) show segmentation of subjects between 'normal' 802 and 'not normal' 804 respectively, for an average waking heart rate of around 80 beats per minute. FIGS. 9(*a*) and 9(*b*) show similar segmentation 902, 904 for a waking heart rate of around 87.7 beats per minute, while the segmentations 1002, 1004 in FIGS. 10(*a*) and 10(*b*) are for an average waking heart rate of around 96 beats per minute.

It is clear from the three sets of charts in FIGS. 8, 9 and 10 that, for each value of average waking heart rate, there is a distinct segmentation between 'normal' and 'not normal' subjects. For example, at around 80 beats per minute, 'normal' subjects are clustered within the metric space in two groups, forming a 'galley'. Conversely, the 'not normal' subjects are clustered within the metric space in a single grouping, corresponding with the 'aisle'. At a heart rate of around 87.7 beats per minute, the 'normal' subjects are distributed in the form of a 'table' within metric space, while the 'not normal' subjects are clustered within an approximate cube shape. Finally, at around 96 beats per minute, the 'normal' subjects are clustered in two connecting perpendicular planes, while again a 'cube-like' structure characterises the distribution of 'not normal' subjects within the metric space.

It can also be inferred from the 'slices' illustrated in FIGS. 8, 9 and 10 that there is an evolution in the partitioning between 'normal' and 'not normal' within the metric space as heart rate increases. The 'galley' at around 80 beats per minute evolves into the 'table' structure at around 87.7 beats per minute, while the 'aisle' structure of 'not normals' expands to occupy the space under the 'table'. This evolution can be seen to continue as average working heart rate increases from around 87.7 beats per minute to 96 beats per minute.

Some embodiments of the invention may be configured to provide additional information in the form of an objective measure of a 'degree' of the subject's state of mental health, e.g. a quantitative answer to the question 'how normal?' (or 'how depressed'?) Considering the normal case, for example, a distance from the normal centroid may be evaluated and used to provide further quantitative information. For a set of metrics m={$m_1$, $m_2$, $m_N$} of dimension N, a distance d from the normal centroid $m_n$={$m_{n,1}$, $m_{n,2}$, ..., $m_{n,N}$} is given by:

$$d = \sum_{k=1}^{N} |m_k - m_{n,k}|$$

The measure d is thus a quantitative indication of how far away the subject is from the 'average' normal subject from the training set.

Figure 11:
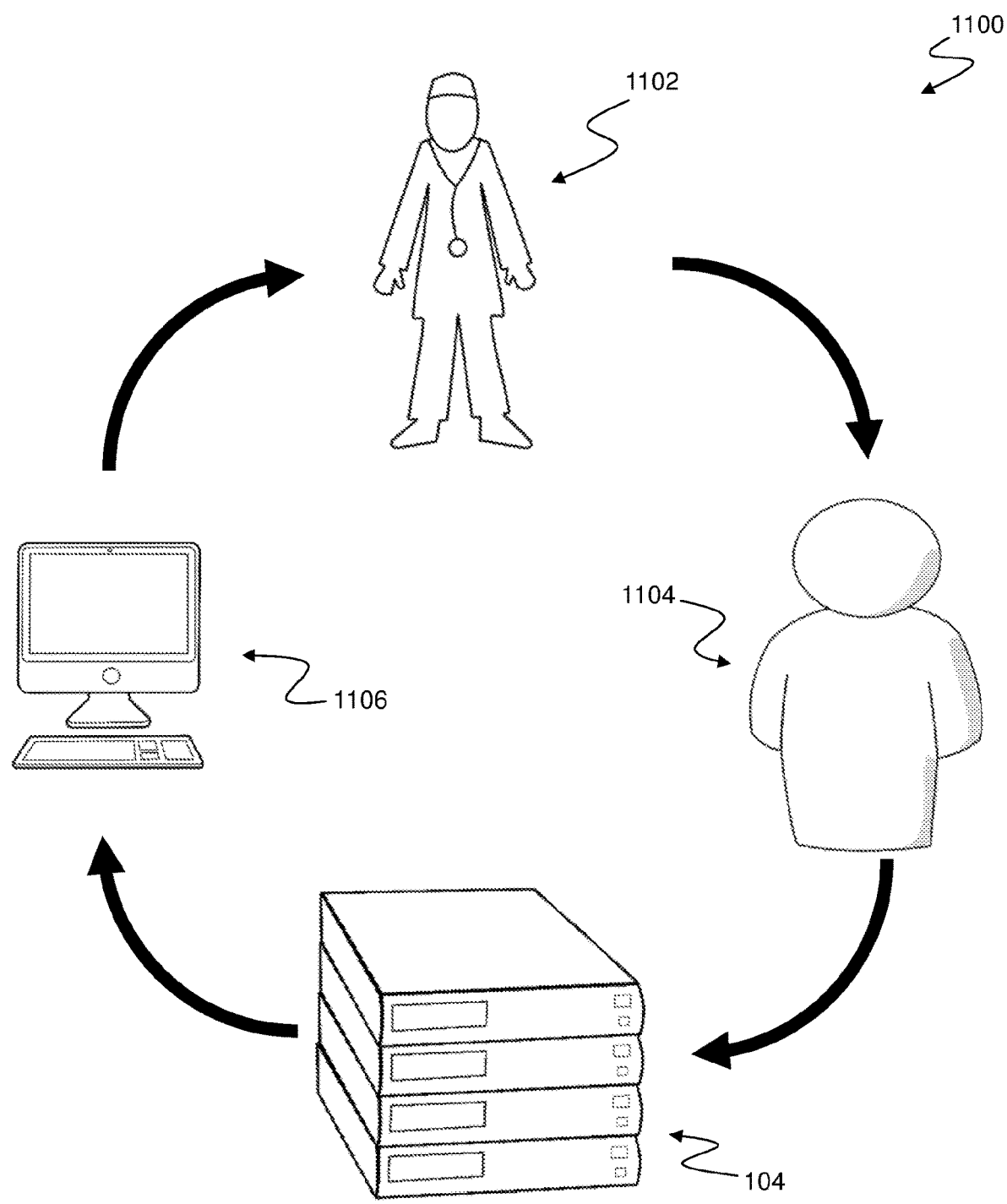
FIG. 11 is a block diagram illustrating a process of evaluation, diagnosis and treatment employing an embodiment of the invention.

Turning now to FIG. 11, there is shown a process 1100 for evaluation, diagnosis and treatment employing an embodiment of the invention 104. The process 1100 involves a clinician 1102, such as a doctor/general practitioner, ordering a test of mental health of a patient using the system 104. At 1104 the patient undergoes heart rate measurement over a suitable period, including a sleeping period, and the data is collected for example via an app on a portable device 110 or an application or web-based interface executing on a PC 112, and then uploaded to the server 104 for analysis.

Once the analysis is complete, the results are stored within secure storage of the server 104, and are made accessible to the clinician 1102 via a secure access interface 1106, such as a web portal. The clinician 1102 is thereby able to review the results of the measurement and analysis, and determine the appropriate next steps in diagnosis and treatment of the patient. For example, if the results are 'normal', and yet the patient is exhibiting continuing adverse symptoms, the clinician 1102 may determine that additional testing or other assessment is required. If the results indicate that the patient is depressed, the clinician may reach a corresponding diagnosis and/or may refer the patient to a specialist, such as a psychologist or psychiatrist, for further assessment and treatment. If the assessment is that the patient is not depressed, but is also not normal, further testing and/or referral may be indicated. These decisions remain in the hands of the clinician 1102, however the assessment performed by the server 104 according to an embodiment of the invention clearly provides a useful, consistent and objective tool to assist the clinician 1102.

Furthermore, if treatment of the patient, for example by counseling or drugs, is prescribed then the cycle of recording 1104, analysis by the server 104, and review 1106 by the clinician 1102 may be repeated while treatment is ongoing. Such ongoing assessment provides a continuing objective measurement of the effectiveness of treatment. If the assessed mental state of the patient improves, for example moving from 'depression' to 'normal' indication, then the treatment may be regarded as successful. If, on the other hand, no objective positive change in the indicated mental state of the patient is observed, the clinician 1102, and/or any specialist to whom the patient may have been referred, may consider adjusting the treatment, for example by changing or supplementing pharmaceutical or counseling options.

In summary, embodiments of the present invention provide methods and systems enabling measurement, monitoring and assessment of mental state, and in particular indications of mental health of individual subjects, via simple and non-invasive heartbeat measurements. Advantageously, measurements may be performed using unobtrusive wearable devices, enabling subjects to go about their normal daily activities. Assessments are automatically generated using computational models, for example executed on a server accessible via the Internet, using a knowledge base comprising expert assessment information.

Services and applications provided in accordance with embodiments of the invention may be available to subjects individually, but may more usefully be made available via health care professionals, such as a patient subject's own doctor. This enables the doctor to instruct the patient in proper operation of the monitoring device, and proper conduct of the heart measurements, and to receive the output indication of the patient's state of mental health directly. Based on this indication, and other patient health information available to the doctor, professional recommendations may be made regarding the possible diagnosis and treatment of any adverse mental health condition from which the patient. In appropriate cases a doctor may elect to refer a patient to a specialist, such as a psychiatrist, for further assessment, testing, diagnosis and/or treatment.

The assessment platform 104 may keep historical records, and make these available via the Internet, such that individuals and/or their supervising doctors can conduct ongoing monitoring of mental health.

Potential benefits of embodiments of the invention include improved and objective identification of individuals who are suffering from, or at risk of, mental health problems, such as depression. The non-invasive and unobtrusive nature of the heart-rate measurements taken using wearable devices ensures a low barrier to compliance, and may enable early detection of potential issues, such that diagnosis and treatment may be undertaken prior to progression of a problem, thus reducing adverse outcomes and health care costs. Accordingly, numerous benefits may be obtained by individuals, healthcare professionals, and by society.

While particular embodiments have been described, by way of example only, a person skilled in the relevant arts will appreciate that a number of variations are possible, within the scope of the present invention. Accordingly, the exemplary embodiments should not be regarded as limiting, but rather the invention is as defined in the claims appended hereto.

The claims defining the invention are as follows:

1. A computer-implemented method of assessing a mental state of a subject, the method comprising:
   receiving a heartbeat record indicative of a heart rate of the subject over a time span which includes a pre-sleep period, a sleep period having a sleep onset time and a sleep conclusion time, and a post-sleep period;
   identifying, within the heartbeat record, at least the sleep onset nine and the sleep conclusion time;
   analysing the heartbeat record using the identified sleep onset time and the sleep conclusion time to determine at least two heart rate metrics, the at least two heart rate metrics including:
     a ratio between mean awake and mean asleep heart rates; and
     a slope of heart rate;
   applying the at least two heart rate metrics to a computational model of a relationship between mental state and heart rate characteristics to generate an indication of mental state based upon the at least two heart rate metrics, the computation model being obtained by applying machine learning to at least two heart rate metrics derived from heart rates measured for subjects in a training set who have been assessed by an expert assessor; and
   providing, as output, the indication of mental state;
   wherein the computational model forms part of a knowledge base including one or more data structures resulting from application of a machine learning algorithm to heart rate metrics computed by processing heartbeat records of the training set of subjects;
   wherein the knowledge base comprises data structures representing one or more classification trees obtained by applying a decision tree learning algorithm over the heart rate metrics computed by processing heartbeat records of the training set of subjects;
   wherein the decision tree learning algorithm is applied to generate two classification tree data structures, which are stored in the knowledge base, and wherein:
   a first classification tree data structure classifies at least one of the at least two heart rate metrics of the subject into 'normal' or 'not normal'; and
   a second classification tree data structure classifies the at least one of the at least two heart rate metrics of the subject into 'depressed' and 'not depressed'.

2. The method of claim 1 wherein the indication of mental state comprises an indication of mental health of the subject.

3. The method of claim 2 wherein the indication of mental health of the subject ix selected from a group comprising at least 'normal' and 'depression'.

4. The method of claim 2 wherein the computational model forms part of a knowledge base, the knowledge base including at least one template heart rate characteristic.

5. The method of claim 4 wherein the at least one template heart rate characteristic is obtained by averaging scaled and normalised heart rate characteristics of the subjects in the training set who have been assessed by an expert assessor as having a common state of mental health.

6. The method of claim 5 wherein the knowledge base comprises a first template heart rate characteristic corresponding with subjects in the training set who have been assessed by the expert assessor as having a normal state of mental health, and a second template heart rate characteristic corresponding with subjects in the training set who have been assessed by the expert assessor as having depression.

7. The method of claim 1, which comprises:
   classifying the subject as 'normal' or 'not normal' by executing the first classification tree; and
   in the event that the subject is classified as 'not normal', classifying the subject as 'depressed' or 'not depressed' by executing the second classification tree.

8. A computer-implemented system for assessing a mental state of a subject, the system comprising:
   at least one microprocessor;
   at least one non-volatile storage device containing a computational model of a relationship between mental state and heart rate characteristics, the computation model being obtained by applying machine learning to at least two heart rate metrics derived from heart rates measured for subjects in a training set who have been assessed by an expert assessor;
   wherein the at least two heart rate metrics include:
     a ratio between mean awake and mean asleep heart rates; and
     a slope of heart rate;
   at least one computer-readable memory device operatively associated with the microprocessor; and
   wherein the memory device contains computer-executable instruction code which, when executed via the microprocessor, causes the microprocessor to effect a method comprising steps of:
   receiving a heartbeat record indicative of a heart rate of the subject over a timespan which includes a pre-sleep period, a sleep period having a sleep onset time and a sleep conclusion time, and a post-sleep period;

identifying, within the heartbeat record, at least the sleep onset time and the sleep conclusion time;
analysing the heartbeat record using the identified sleep onset time and the sleep conclusion time to determine at least two heart rate metrics;
applying the at least two heart rate metrics to the computational model to generate an indication of mental state based upon the at least two heart rate metrics; and
providing, via the input/output interface, the indication of the mental state of the subject
wherein the computational model forms part of a knowledge base including one or more data structures resulting from application of a machine learning algorithm to heart rate metrics computed by processing heartbeat records of the training set of subjects;
wherein the knowledge base comprises data structures representing one or more classification trees obtained by applying a decision tree learning algorithm over the heart rate metrics computed by processing heartbeat records of the training set of subjects;
wherein the decision tree learning algorithm is applied to generate two classification tree data structures, which are stored in the knowledge base, and wherein:
a first classification tree data structure classifies at least one of the at least two heart rate metrics of the subject into 'normal' or 'not normal'; and
a second classification tree data structure classifies at least one of the at least two heart rate metrics of the subject into 'depressed' and 'not depressed'.

9. The system of claim 8 wherein the heartbeat record of the subject is obtained via a heart rate monitor device worn by the subject during the timespan including the pre-sleep period, the sleep period and the post-sleep period.

10. The system of claim 9 wherein the heartbeat monitor comprises a communications interface configured for communication with a network-connected device.

11. The system of claim 10 wherein the heartbeat record is received via an input/output interface comprising a network interface providing access to a wide area network, and the heartbeat record is received via the wide area network from the network-connected device of the subject.

12. The method of claim 1, wherein the method includes determining at least four heart rate metrics, the at least four heart rate metrics including:
a mean awake heart rate;
the ratio of heart rates;
a first slope metric; and
a second slope metric.

13. The system of claim 8, wherein the system includes determining a least four heart rate metrics, the at least four heart rate metrics including:
a mean awake heart rate;
the ratio of heart rates;
a first slope metric; and
a second slope metric.

* * * * *